US010801018B2

(12) United States Patent
Montaño-Suarez et al.

(10) Patent No.: US 10,801,018 B2
(45) Date of Patent: Oct. 13, 2020

(54) REDUCED IMMUNOGENIC PROTEINS FOR LYSOSOMAL STORAGE DISORDERS

(71) Applicant: Saint Louis University, St. Louis, MO (US)

(72) Inventors: Adriana M. Montaño-Suarez, St. Louis, MO (US); Angela Sosa-Molano, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 16/599,730

(22) Filed: Oct. 11, 2019

(65) Prior Publication Data

US 2020/0032229 A1 Jan. 30, 2020

Related U.S. Application Data

(62) Division of application No. 15/411,797, filed on Jan. 20, 2017, now Pat. No. 10,472,615.

(60) Provisional application No. 62/281,611, filed on Jan. 21, 2016.

(51) Int. Cl.
*C12N 9/16* (2006.01)
*A61K 38/00* (2006.01)

(52) U.S. Cl.
CPC ........ *C12N 9/16* (2013.01); *C12Y 301/06004* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,929,796 | B1 | 8/2005 | Conti-Fine |
| 2007/0105122 | A1 | 5/2007 | Ota et al. |
| 2011/0177107 | A1 | 7/2011 | Howard |
| 2013/0202633 | A1 | 8/2013 | Montano-Suarez |

FOREIGN PATENT DOCUMENTS

| | | |
|---|---|---|
| WO | 2012012718 A2 | 1/2012 |
| WO | 2013119715 A1 | 8/2013 |

OTHER PUBLICATIONS

Dvorak-Ewell et al., Enzyme replacenment in a human model of mucopolysaccharidosis IVA in vitro and its biodistribution in the cartilage of wild type mice. PLoS One, 2010, vol. 5, No. 8, pp. e12194.
Lee et al., Development of a less immunogenic protein for enzyme replacement therapy of Morquio syndrome type A disease, Molecular Genetics and Metabolis, 2015, vol. 114, No. 2, pp. S71.
Lee et al., Development of a less immunogenic protein for enzyme replacement therapy of Morquio a Disease; The 8th Annual Pediatric Science Day Symposium. Saint Louis University, Si Louis, MO., 2014, pp. 11.
Olarte et al., Computational approach for the design of a less immunogenic GALNS enzyme, Molecular Genetics and Metabolism, 2014, vol. 111, No. 2, pp. S82.
Peters et al., The design and implementation of the Immune epitope database and analysis resource. Immunogenetics, 2005, vol. 57, No. 5, pp. 326-336.
Rivera-Colon et al., The structure of human GALNS reveals the molecular basis for Mucopolysaccharidosis IV, A. J. Mol. Biol. Epub, 2012, vol. 423, No. 5, pp. 736-751.
Sosa et al., Identification of Immunodominant Epitopes in N-Acetylgalactosamine 6-Sulfate Sulfatase (GALNS) for Designing an Effective Peptide-Based Immunotherapy. Molecular Genetics and metabolism, 2012, vol. 105, No. 2, pp. S58.
Sosa et al., Towards the development of a less immunogenic protein for enzyme replacement therapy of Morquio disease type Molecular Genetics and Metabolism, 2013, vol. 108, No. 2, pp. S87.
Tomatsu et al., Enhancement of drug delivery: enzyme-replacement therapy for murine Morqulo A syndrome. Mol. Ther., 2010, vol. 18, No. 6, pp. 1094-1102.

*Primary Examiner* — Suzanne M Noakes
(74) *Attorney, Agent, or Firm* — Stinson Leonard Street

(57) ABSTRACT

Disclosed are methods and compositions for reduced immunogenic proteins used in enzyme replacement therapy for lysosomal storage disorders. More specifically disclosed are genetically engineered variants of N-acetylgalactosamine-6-sulfatase (GALNS), which are less immunogenetic then wild-type GALNS, but maintain enzymatic activity, and may be used to treat Mucopolysaccharidosis IVA (Morquio A disease, MPS IVA).

9 Claims, 20 Drawing Sheets
(20 of 20 Drawing Sheet(s) Filed in Color)
Specification includes a Sequence Listing.

| GALNS Immunodominant peptides | | |
|---|---|---|
| Peptide No | GALNS region | Sequence |
| C4 | 163-182 | PNCHFGPYDNKARPNIPVYR (SEQ ID NO:9) |
| E8 | 226-245 | FFLYWAVDATHAPVYASKPF (SEQ ID NO:10) |
| I10 | 473-492 | QQHQEALVPAQPQLNVTNWA (SEQ ID NO:11) |

GALNS

C4-N6 superimposed onto GALNS

E8-N13

E8-N13 superimposed onto GALNS Model 1

I10-N14

I10-N14 Superimposed onto GALNS

GALNS-242 superimposed onto GALNS Model 1

GALNS-201

GALNS-201 superimposed onto GALNS Model 1

GALNS-315

GALNS-315 superimposed onto GALNS Model 1

GALNS-231

GALNS-231 superimposed on GALNS Model 1

SEQUENCE LISTING

```
<160> NUMBER OF SEQ ID NOS: 41

<210> SEQ ID NO 1
<211> LENGTH: 522
<212> TYPE: PRT
<213> ORGANISM: Homo sapiens

<400> SEQUENCE: 1

Met Ala Ala Val Val Ala Ala Thr Arg Trp Trp Gln Leu Leu Leu Val
1               5                   10                  15

Leu Ser Ala Ala Gly Met Gly Ala Ser Gly Ala Pro Gln Pro Pro Asn
            20                  25                  30

Ile Leu Leu Leu Leu Met Asp Asp Met Gly Trp Gly Asp Leu Gly Val
        35                  40                  45

Tyr Gly Glu Pro Ser Arg Glu Thr Pro Asn Leu Asp Arg Met Ala Ala
    50                  55                  60

Glu Gly Leu Leu Phe Pro Asn Phe Tyr Ser Ala Asn Pro Leu Cys Ser
65                  70                  75                  80

Pro Ser Arg Ala Ala Leu Leu Thr Gly Arg Leu Pro Ile Arg Asn Gly
                85                  90                  95

Phe Tyr Thr Thr Asn Ala His Ala Arg Asn Ala Tyr Thr Pro Gln Glu
            100                 105                 110

Ile Val Gly Gly Ile Pro Asp Ser Glu Gln Leu Leu Pro Glu Leu Leu
        115                 120                 125

Lys Lys Ala Gly Tyr Val Ser Lys Ile Val Gly Lys Trp His Leu Gly
    130                 135                 140

His Arg Pro Gln Phe His Pro Leu Lys His Gly Phe Asp Glu Trp Phe
145                 150                 155                 160

Gly Ser Pro Asn Cys His Phe Gly Pro Tyr Asp Asn Lys Ala Arg Pro
                165                 170                 175
```

```
Asn Ile Pro Val Tyr Arg Asp Trp Glu Met Val Gly Arg Tyr Tyr Glu
                180                 185                 190

Glu Phe Pro Ile Asn Leu Lys Thr Gly Glu Ala Asn Leu Thr Gln Ile
            195                 200                 205

Tyr Leu Gln Glu Ala Leu Asp Phe Ile Lys Arg Gln Ala Arg His His
        210                 215                 220

Pro Phe Phe Leu Tyr Trp Ala Val Asp Ala Thr His Ala Pro Val Tyr
225                 230                 235                 240

Ala Ser Lys Pro Phe Leu Gly Thr Ser Gln Arg Gly Arg Tyr Gly Asp
                245                 250                 255

Ala Val Arg Glu Ile Asp Asp Ser Ile Gly Lys Ile Leu Glu Leu Leu
            260                 265                 270

Gln Asp Leu His Val Ala Asp Asn Thr Phe Val Phe Phe Thr Ser Asp
        275                 280                 285

Asn Gly Ala Ala Leu Ile Ser Ala Pro Glu Gln Gly Gly Ser Asn Gly
290                 295                 300

Pro Phe Leu Cys Gly Lys Gln Thr Thr Phe Glu Gly Gly Met Arg Glu
305                 310                 315                 320

Pro Ala Leu Ala Trp Trp Pro Gly His Val Thr Ala Gly Gln Val Ser
                325                 330                 335

His Gln Leu Gly Ser Ile Met Asp Leu Phe Thr Thr Ser Leu Ala Leu
            340                 345                 350

Ala Gly Leu Thr Pro Pro Ser Asp Arg Ala Ile Asp Gly Leu Asn Leu
        355                 360                 365

Leu Pro Thr Leu Leu Gln Gly Arg Leu Met Asp Arg Pro Ile Phe Tyr
370                 375                 380

Tyr Arg Gly Asp Thr Leu Met Ala Ala Thr Leu Gly Gln His Lys Ala
385                 390                 395                 400

His Phe Trp Thr Trp Thr Asn Ser Trp Glu Asn Phe Arg Gln Gly Ile
                405                 410                 415

Asp Phe Cys Pro Gly Gln Asn Val Ser Gly Val Thr Thr His Asn Leu
            420                 425                 430

Glu Asp His Thr Lys Leu Pro Leu Ile Phe His Leu Gly Arg Asp Pro
        435                 440                 445

Gly Glu Arg Phe Pro Leu Ser Phe Ala Ser Ala Glu Tyr Gln Glu Ala
450                 455                 460

Leu Ser Arg Ile Thr Ser Val Val Gln Gln His Gln Glu Ala Leu Val
465                 470                 475                 480

Pro Ala Gln Pro Gln Leu Asn Val Cys Asn Trp Ala Val Met Asn Trp
                485                 490                 495

Ala Pro Pro Gly Cys Glu Lys Leu Gly Lys Cys Leu Thr Pro Pro Glu
            500                 505                 510

Ser Ile Pro Lys Lys Cys Leu Trp Ser His
        515                 520

<210> SEQ ID NO 2
<211> LENGTH: 522
<212> TYPE: PRT
<213> ORGANISM: Homo sapiens

<400> SEQUENCE: 2

Met Ala Ala Val Val Ala Ala Thr Arg Trp Trp Gln Leu Leu Leu Val
1               5                   10                  15

Leu Ser Ala Ala Gly Met Gly Ala Ser Gly Ala Pro Gln Pro Pro Asn
            20                  25                  30
```

```
Ile Leu Leu Leu Leu Met Asp Asp Met Gly Trp Gly Asp Leu Gly Val
            35                  40                  45
Tyr Gly Glu Pro Ser Arg Glu Thr Pro Asn Leu Asp Arg Met Ala Ala
 50                      55                  60
Glu Gly Leu Leu Phe Pro Asn Phe Tyr Ser Ala Asn Pro Leu Cys Ser
 65                  70                  75                  80
Pro Ser Arg Ala Ala Leu Leu Thr Gly Arg Leu Pro Ile Arg Asn Gly
                 85                  90                  95
Phe Tyr Thr Thr Asn Ala His Ala Arg Asn Ala Tyr Thr Pro Gln Glu
                 100                 105                 110
Ile Val Gly Gly Ile Pro Asp Ser Glu Gln Leu Leu Pro Glu Leu Leu
             115                 120                 125
Lys Lys Ala Gly Tyr Val Ser Lys Ile Val Gly Lys Trp His Leu Gly
         130                 135                 140
His Arg Pro Gln Phe His Pro Leu Lys His Gly Phe Asp Glu Trp Phe
145                 150                 155                 160
Gly Ser Pro Asn Cys His Phe Gly Pro Tyr Asp Asn Lys Ile Arg Gly
                 165                 170                 175
Gln Ile Pro Val Tyr Arg Asp Trp Glu Met Val Gly Arg Tyr Tyr Glu
             180                 185                 190
Glu Phe Pro Ile Asn Leu Lys Thr Gly Glu Ala Asn Leu Thr Gln Ile
         195                 200                 205
Tyr Leu Gln Glu Ala Leu Asp Phe Ile Lys Arg Gln Ala Arg His His
     210                 215                 220
Pro Phe Phe Leu Tyr Trp Ala Val Asp Ala Thr His Ala Pro Val Tyr
225                 230                 235                 240
Ala Ser Lys Pro Phe Leu Gly Thr Ser Gln Arg Gly Arg Tyr Gly Asp
                 245                 250                 255
Ala Val Arg Glu Ile Asp Asp Ser Ile Gly Lys Ile Leu Glu Leu Leu
             260                 265                 270
Gln Asp Leu His Val Ala Asp Asn Thr Phe Val Phe Phe Thr Ser Asp
         275                 280                 285
Asn Gly Ala Ala Leu Ile Ser Ala Pro Glu Gln Gly Gly Ser Asn Gly
     290                 295                 300
Pro Phe Leu Cys Gly Lys Gln Thr Thr Phe Glu Gly Gly Met Arg Glu
305                 310                 315                 320
Pro Ala Leu Ala Trp Trp Pro Gly His Val Thr Ala Gly Gln Val Ser
                 325                 330                 335
His Gln Leu Gly Ser Ile Met Asp Leu Phe Thr Thr Ser Leu Ala Leu
             340                 345                 350
Ala Gly Leu Thr Pro Pro Ser Asp Arg Ala Ile Asp Gly Leu Asn Leu
         355                 360                 365
Leu Pro Thr Leu Leu Gln Gly Arg Leu Met Asp Arg Pro Ile Phe Tyr
     370                 375                 380
Tyr Arg Gly Asp Thr Leu Met Ala Ala Thr Leu Gly Gln His Lys Ala
385                 390                 395                 400
His Phe Trp Thr Trp Thr Asn Ser Trp Glu Asn Phe Arg Gln Gly Ile
                 405                 410                 415
Asp Phe Cys Pro Gly Gln Asn Val Ser Gly Val Thr His Asn Leu
             420                 425                 430
Glu Asp His Thr Lys Leu Pro Leu Ile Phe His Leu Gly Arg Asp Pro
         435                 440                 445
```

Gly Glu Arg Phe Pro Leu Ser Phe Ala Ser Ala Glu Tyr Gln Glu Ala
    450                 455                 460

Leu Ser Arg Ile Thr Ser Val Val Gln Gln His Gln Glu Ala Leu Val
465                 470                 475                 480

Pro Ala Gln Pro Gln Leu Asn Val Cys Asn Trp Ala Val Met Asn Trp
                    485                 490                 495

Ala Pro Pro Gly Cys Glu Lys Leu Gly Lys Cys Leu Thr Pro Pro Glu
                500                 505                 510

Ser Ile Pro Lys Lys Cys Leu Trp Ser His
                515                 520

<210> SEQ ID NO 3
<211> LENGTH: 522
<212> TYPE: PRT
<213> ORGANISM: Homo sapiens

<400> SEQUENCE: 3

Met Ala Ala Val Val Ala Ala Thr Arg Trp Trp Gln Leu Leu Leu Val
1               5                   10                  15

Leu Ser Ala Ala Gly Met Gly Ala Ser Gly Ala Pro Gln Pro Pro Asn
            20                  25                  30

Ile Leu Leu Leu Leu Met Asp Asp Met Gly Trp Gly Asp Leu Gly Val
        35                  40                  45

Tyr Gly Glu Pro Ser Arg Glu Thr Pro Asn Leu Asp Arg Met Ala Ala
    50                  55                  60

Glu Gly Leu Leu Phe Pro Asn Phe Tyr Ser Ala Asn Pro Leu Cys Ser
65                  70                  75                  80

Pro Ser Arg Ala Ala Leu Leu Thr Gly Arg Leu Pro Ile Arg Asn Gly
                85                  90                  95

Phe Tyr Thr Thr Asn Ala His Ala Arg Asn Ala Tyr Thr Pro Gln Glu
            100                 105                 110

Ile Val Gly Gly Ile Pro Asp Ser Glu Gln Leu Leu Pro Glu Leu Leu
        115                 120                 125

Lys Lys Ala Gly Tyr Val Ser Lys Ile Val Gly Lys Trp His Leu Gly
    130                 135                 140

His Arg Pro Gln Phe His Pro Leu Lys His Gly Phe Asp Glu Trp Phe
145                 150                 155                 160

Gly Ser Pro Asn Cys His Phe Gly Pro Tyr Asp Asn Lys Ala Arg Pro
                165                 170                 175

Asn Ile Pro Val Tyr Arg Asp Trp Glu Met Val Gly Arg Tyr Tyr Glu
            180                 185                 190

Glu Phe Pro Ile Asn Leu Lys Thr Gly Glu Ala Asn Leu Thr Gln Ile
        195                 200                 205

Tyr Leu Gln Glu Ala Leu Asp Phe Ile Lys Arg Gln Ala Arg His His
    210                 215                 220

Pro Phe Phe Leu Ile Trp Ala Val Asp Leu Thr His Leu Pro Val Tyr
225                 230                 235                 240

Ala Ser Lys Pro Phe Leu Gly Thr Ser Gln Arg Gly Arg Tyr Gly Asp
                245                 250                 255

Ala Val Arg Glu Ile Asp Asp Ser Ile Gly Lys Ile Leu Glu Leu Leu
            260                 265                 270

Gln Asp Leu His Val Ala Asp Asn Thr Phe Val Phe Phe Thr Ser Asp
        275                 280                 285

Asn Gly Ala Ala Leu Ile Ser Ala Pro Glu Gln Gly Gly Ser Asn Gly
    290                 295                 300

```
Pro Phe Leu Cys Gly Lys Gln Thr Thr Phe Glu Gly Met Arg Glu
305                 310                 315                 320

Pro Ala Leu Ala Trp Trp Pro Gly His Val Thr Ala Gly Gln Val Ser
            325                 330                 335

His Gln Leu Gly Ser Ile Met Asp Leu Phe Thr Thr Ser Leu Ala Leu
                340                 345                 350

Ala Gly Leu Thr Pro Pro Ser Asp Arg Ala Ile Asp Gly Leu Asn Leu
            355                 360                 365

Leu Pro Thr Leu Leu Gln Gly Arg Leu Met Asp Arg Pro Ile Phe Tyr
        370                 375                 380

Tyr Arg Gly Asp Thr Leu Met Ala Ala Thr Leu Gly Gln His Lys Ala
385                 390                 395                 400

His Phe Trp Thr Trp Thr Asn Ser Trp Glu Asn Phe Arg Gln Gly Ile
                405                 410                 415

Asp Phe Cys Pro Gly Gln Asn Val Ser Gly Val Thr Thr His Asn Leu
            420                 425                 430

Glu Asp His Thr Lys Leu Pro Leu Ile Phe His Leu Gly Arg Asp Pro
                435                 440                 445

Gly Glu Arg Phe Pro Leu Ser Phe Ala Ser Ala Glu Tyr Gln Glu Ala
        450                 455                 460

Leu Ser Arg Ile Thr Ser Val Val Gln Gln His Gln Glu Ala Leu Val
465                 470                 475                 480

Pro Ala Gln Pro Gln Leu Asn Val Cys Asn Trp Ala Val Met Asn Trp
                485                 490                 495

Ala Pro Pro Gly Cys Glu Lys Leu Gly Lys Cys Leu Thr Pro Pro Glu
            500                 505                 510

Ser Ile Pro Lys Lys Cys Leu Trp Ser His
                515                 520

<210> SEQ ID NO 4
<211> LENGTH: 522
<212> TYPE: PRT
<213> ORGANISM: Homo sapiens

<400> SEQUENCE: 4

Met Ala Ala Val Val Ala Ala Thr Arg Trp Trp Gln Leu Leu Leu Val
1               5                   10                  15

Leu Ser Ala Ala Gly Met Gly Ala Ser Gly Ala Pro Gln Pro Pro Asn
            20                  25                  30

Ile Leu Leu Leu Met Asp Asp Met Gly Trp Gly Asp Leu Gly Val
        35                  40                  45

Tyr Gly Glu Pro Ser Arg Glu Thr Pro Asn Leu Asp Arg Met Ala Ala
    50                  55                  60

Glu Gly Leu Leu Phe Pro Asn Phe Tyr Ser Ala Asn Pro Leu Cys Ser
65                  70                  75                  80

Pro Ser Arg Ala Ala Leu Leu Thr Gly Arg Leu Pro Ile Arg Asn Gly
                85                  90                  95

Phe Tyr Thr Thr Asn Ala His Ala Arg Asn Ala Tyr Thr Pro Gln Glu
            100                 105                 110

Ile Val Gly Gly Ile Pro Asp Ser Glu Gln Leu Leu Pro Glu Leu Leu
        115                 120                 125

Lys Lys Ala Gly Tyr Val Ser Lys Ile Val Gly Lys Trp His Leu Gly
    130                 135                 140

His Arg Pro Gln Phe His Pro Leu Lys His Gly Phe Asp Glu Trp Phe
```

```
145                 150                 155                 160
Gly Ser Pro Asn Cys His Phe Gly Pro Tyr Asp Asn Lys Ala Arg Pro
                165                 170                 175

Asn Ile Pro Val Tyr Arg Asp Trp Glu Met Val Gly Arg Tyr Tyr Glu
            180                 185                 190

Glu Phe Pro Ile Asn Leu Lys Thr Gly Glu Ala Asn Leu Thr Gln Ile
            195                 200                 205

Tyr Leu Gln Glu Ala Leu Asp Phe Ile Lys Arg Gln Ala Arg His His
        210                 215                 220

Pro Phe Phe Leu Tyr Trp Ala Val Asp Ala Thr His Ala Pro Val Tyr
225                 230                 235                 240

Ala Ser Lys Pro Phe Leu Gly Thr Ser Gln Arg Gly Arg Tyr Gly Asp
                245                 250                 255

Ala Val Arg Glu Ile Asp Asp Ser Ile Gly Lys Ile Leu Glu Leu Leu
            260                 265                 270

Gln Asp Leu His Val Ala Asp Asn Thr Phe Val Phe Thr Ser Asp
        275                 280                 285

Asn Gly Ala Ala Leu Ile Ser Ala Pro Glu Gln Gly Gly Ser Asn Gly
        290                 295                 300

Pro Phe Leu Cys Gly Lys Gln Thr Thr Phe Glu Gly Gly Met Arg Glu
305                 310                 315                 320

Pro Ala Leu Ala Trp Trp Pro Gly His Val Thr Ala Gly Gln Val Ser
                325                 330                 335

His Gln Leu Gly Ser Ile Met Asp Leu Phe Thr Thr Ser Leu Ala Leu
            340                 345                 350

Ala Gly Leu Thr Pro Pro Ser Asp Arg Ala Ile Asp Gly Leu Asn Leu
        355                 360                 365

Leu Pro Thr Leu Leu Gln Gly Arg Leu Met Asp Arg Pro Ile Phe Tyr
        370                 375                 380

Tyr Arg Gly Asp Thr Leu Met Ala Ala Thr Leu Gly Gln His Lys Ala
385                 390                 395                 400

His Phe Trp Thr Trp Thr Asn Ser Trp Glu Asn Phe Arg Gln Gly Ile
                405                 410                 415

Asp Phe Cys Pro Gly Gln Asn Val Ser Gly Val Thr His His Asn Leu
            420                 425                 430

Glu Asp His Thr Lys Leu Pro Leu Ile Phe His Leu Gly Arg Asp Pro
        435                 440                 445

Gly Glu Arg Phe Pro Leu Ser Phe Ala Ser Ala Glu Tyr Gln Glu Ala
        450                 455                 460

Leu Ser Arg Ile Thr Ser Val Val Gln Gln His Gln Glu Ala Leu Val
465                 470                 475                 480

Gly Ile Gln Gly Gln Leu Asn Val Cys Asn Trp Ala Val Met Asn Trp
                485                 490                 495

Ala Pro Pro Gly Cys Glu Lys Leu Gly Lys Cys Leu Thr Pro Pro Glu
            500                 505                 510

Ser Ile Pro Lys Lys Cys Leu Trp Ser His
        515                 520

<210> SEQ ID NO 5
<211> LENGTH: 522
<212> TYPE: PRT
<213> ORGANISM: Homo sapiens

<400> SEQUENCE: 5
```

```
Met Ala Ala Val Val Ala Ala Thr Arg Trp Trp Gln Leu Leu Leu Val
1               5                   10                  15

Leu Ser Ala Ala Gly Met Gly Ala Ser Gly Ala Pro Gln Pro Pro Asn
            20                  25                  30

Ile Leu Leu Leu Leu Met Asp Asp Met Gly Trp Gly Asp Leu Gly Val
                35                  40                  45

Tyr Gly Glu Pro Ser Arg Glu Thr Pro Asn Leu Asp Arg Met Ala Ala
    50                  55                  60

Glu Gly Leu Leu Phe Pro Asn Phe Tyr Ser Ala Asn Pro Leu Cys Ser
65                  70                  75                  80

Pro Ser Arg Ala Ala Leu Leu Thr Gly Arg Leu Pro Ile Arg Asn Gly
                85                  90                  95

Phe Tyr Thr Thr Asn Ala His Ala Arg Asn Ala Tyr Thr Pro Gln Glu
                100                 105                 110

Ile Val Gly Gly Ile Pro Asp Ser Glu Gln Leu Leu Pro Glu Leu Leu
                115                 120                 125

Lys Lys Ala Gly Tyr Val Ser Lys Ile Val Gly Lys Trp His Leu Gly
    130                 135                 140

His Arg Pro Gln Phe His Pro Leu Lys His Gly Phe Asp Glu Trp Phe
145                 150                 155                 160

Gly Ser Pro Asn Cys His Phe Gly Pro Tyr Asp Asn Lys Ile Arg Gly
                165                 170                 175

Gln Ile Pro Val Tyr Arg Asp Trp Glu Met Val Gly Arg Tyr Tyr Glu
                180                 185                 190

Glu Phe Pro Ile Asn Leu Lys Thr Gly Glu Ala Asn Leu Thr Gln Ile
                195                 200                 205

Tyr Leu Gln Glu Ala Leu Asp Phe Ile Lys Arg Gln Ala Arg His His
    210                 215                 220

Pro Phe Phe Leu Tyr Trp Ala Val Asp Ala Thr His Ala Pro Val Tyr
225                 230                 235                 240

Ala Ser Lys Pro Phe Leu Gly Thr Ser Gln Arg Gly Arg Tyr Gly Asp
                245                 250                 255

Ala Val Arg Glu Ile Asp Asp Ser Ile Gly Lys Ile Leu Glu Leu Leu
                260                 265                 270

Gln Asp Leu His Val Ala Asp Asn Thr Phe Val Phe Phe Thr Ser Asp
    275                 280                 285

Asn Gly Ala Ala Leu Ile Ser Ala Pro Glu Gln Gly Gly Ser Asn Gly
                290                 295                 300

Pro Phe Leu Cys Gly Lys Gln Thr Thr Phe Glu Gly Gly Met Arg Glu
305                 310                 315                 320

Pro Ala Leu Ala Trp Trp Pro Gly His Val Thr Ala Gly Gln Val Ser
                325                 330                 335

His Gln Leu Gly Ser Ile Met Asp Leu Phe Thr Thr Ser Leu Ala Leu
                340                 345                 350

Ala Gly Leu Thr Pro Pro Ser Asp Arg Ala Ile Asp Gly Leu Asn Leu
                355                 360                 365

Leu Pro Thr Leu Leu Gln Gly Arg Leu Met Asp Arg Pro Ile Phe Tyr
    370                 375                 380

Tyr Arg Gly Asp Thr Leu Met Ala Ala Thr Leu Gly Gln His Lys Ala
385                 390                 395                 400

His Phe Trp Thr Trp Thr Asn Ser Trp Glu Asn Phe Arg Gln Gly Ile
                405                 410                 415

Asp Phe Cys Pro Gly Gln Asn Val Ser Gly Val Thr Thr His Asn Leu
```

```
                    420                 425                 430
Glu Asp His Thr Lys Leu Pro Leu Ile Phe His Leu Gly Arg Asp Pro
                435                 440                 445

Gly Glu Arg Phe Pro Leu Ser Phe Ala Ser Ala Glu Tyr Gln Glu Ala
            450                 455                 460

Leu Ser Arg Ile Thr Ser Val Val Gln Gln His Gln Glu Ala Leu Val
465                 470                 475                 480

Gly Ile Gln Gly Gln Leu Asn Val Cys Asn Trp Ala Val Met Asn Trp
                485                 490                 495

Ala Pro Pro Gly Cys Glu Lys Leu Gly Lys Cys Leu Thr Pro Pro Glu
            500                 505                 510

Ser Ile Pro Lys Lys Cys Leu Trp Ser His
                515                 520

<210> SEQ ID NO 6
<211> LENGTH: 522
<212> TYPE: PRT
<213> ORGANISM: Homo sapiens

<400> SEQUENCE: 6

Met Ala Ala Val Val Ala Ala Thr Arg Trp Trp Gln Leu Leu Leu Val
1               5                   10                  15

Leu Ser Ala Ala Gly Met Gly Ala Ser Gly Ala Pro Gln Pro Pro Asn
            20                  25                  30

Ile Leu Leu Leu Leu Met Asp Asp Met Gly Trp Gly Asp Leu Gly Val
        35                  40                  45

Tyr Gly Glu Pro Ser Arg Glu Thr Pro Asn Leu Asp Arg Met Ala Ala
    50                  55                  60

Glu Gly Leu Leu Phe Pro Asn Phe Tyr Ser Ala Asn Pro Leu Cys Ser
65                  70                  75                  80

Pro Ser Arg Ala Ala Leu Leu Thr Gly Arg Leu Pro Ile Arg Asn Gly
                85                  90                  95

Phe Tyr Thr Thr Asn Ala His Ala Arg Asn Ala Tyr Thr Pro Gln Glu
            100                 105                 110

Ile Val Gly Gly Ile Pro Asp Ser Glu Gln Leu Leu Pro Glu Leu Leu
        115                 120                 125

Lys Lys Ala Gly Tyr Val Ser Lys Ile Val Gly Lys Trp His Leu Gly
    130                 135                 140

His Arg Pro Gln Phe His Pro Leu Lys His Gly Phe Asp Glu Trp Phe
145                 150                 155                 160

Gly Ser Pro Asn Cys His Phe Gly Pro Tyr Asp Asn Lys Ile Arg Gly
                165                 170                 175

Gln Ile Pro Val Tyr Arg Asp Trp Glu Met Val Gly Arg Tyr Tyr Glu
            180                 185                 190

Glu Phe Pro Ile Asn Leu Lys Thr Gly Glu Ala Asn Leu Thr Gln Ile
        195                 200                 205

Tyr Leu Gln Glu Ala Leu Asp Phe Ile Lys Arg Gln Ala Arg His His
    210                 215                 220

Pro Phe Phe Leu Ile Trp Ala Val Asp Leu Thr His Ile Pro Val Tyr
225                 230                 235                 240

Ala Ser Lys Pro Phe Leu Gly Thr Ser Gln Arg Gly Arg Tyr Gly Asp
                245                 250                 255

Ala Val Arg Glu Ile Asp Asp Ser Ile Gly Lys Ile Leu Glu Leu Leu
            260                 265                 270
```

Gln Asp Leu His Val Ala Asp Asn Thr Phe Val Phe Thr Ser Asp
            275                 280                 285

Asn Gly Ala Ala Leu Ile Ser Ala Pro Glu Gln Gly Gly Ser Asn Gly
    290                 295                 300

Pro Phe Leu Cys Gly Lys Gln Thr Thr Phe Glu Gly Gly Met Arg Glu
305                 310                 315                 320

Pro Ala Leu Ala Trp Trp Pro Gly His Val Thr Ala Gly Gln Val Ser
                325                 330                 335

His Gln Leu Gly Ser Ile Met Asp Leu Phe Thr Thr Ser Leu Ala Leu
            340                 345                 350

Ala Gly Leu Thr Pro Pro Ser Asp Arg Ala Ile Asp Gly Leu Asn Leu
        355                 360                 365

Leu Pro Thr Leu Leu Gln Gly Arg Leu Met Asp Arg Pro Ile Phe Tyr
    370                 375                 380

Tyr Arg Gly Asp Thr Leu Met Ala Ala Thr Leu Gly Gln His Lys Ala
385                 390                 395                 400

His Phe Trp Thr Trp Thr Asn Ser Trp Glu Asn Phe Arg Gln Gly Ile
                405                 410                 415

Asp Phe Cys Pro Gly Gln Asn Val Ser Gly Val Thr Thr His Asn Leu
            420                 425                 430

Glu Asp His Thr Lys Leu Pro Leu Ile Phe His Leu Gly Arg Asp Pro
        435                 440                 445

Gly Glu Arg Phe Pro Leu Ser Phe Ala Ser Ala Glu Tyr Gln Glu Ala
    450                 455                 460

Leu Ser Arg Ile Thr Ser Val Val Gln Gln His Gln Glu Ala Leu Val
465                 470                 475                 480

Gly Ile Gln Gly Gln Leu Asn Val Cys Asn Trp Ala Val Met Asn Trp
                485                 490                 495

Ala Pro Pro Gly Cys Glu Lys Leu Gly Lys Cys Leu Thr Pro Pro Glu
            500                 505                 510

Ser Ile Pro Lys Lys Cys Leu Trp Ser His
        515                 520

<210> SEQ ID NO 7
<211> LENGTH: 522
<212> TYPE: PRT
<213> ORGANISM: Homo sapiens

<400> SEQUENCE: 7

Met Ala Ala Val Val Ala Ala Thr Arg Trp Trp Gln Leu Leu Leu Val
1               5                   10                  15

Leu Ser Ala Ala Gly Met Gly Ala Ser Gly Ala Pro Gln Pro Pro Asn
            20                  25                  30

Ile Leu Leu Leu Leu Met Asp Asp Met Gly Trp Gly Asp Leu Gly Val
        35                  40                  45

Tyr Gly Glu Pro Ser Arg Glu Thr Pro Asn Leu Asp Arg Met Ala Ala
    50                  55                  60

Glu Gly Leu Leu Phe Pro Asn Phe Tyr Ser Ala Asn Pro Leu Cys Ser
65                  70                  75                  80

Pro Ser Arg Ala Ala Leu Leu Thr Gly Arg Leu Pro Ile Arg Asn Gly
                85                  90                  95

Phe Tyr Thr Thr Asn Ala His Ala Arg Asn Ala Tyr Thr Pro Gln Glu
            100                 105                 110

Ile Val Gly Gly Ile Pro Asp Ser Glu Gln Leu Leu Pro Glu Leu Leu
        115                 120                 125

Lys Lys Ala Gly Tyr Val Ser Lys Ile Val Gly Lys Trp His Leu Gly
    130                 135                 140

His Arg Pro Gln Phe His Pro Leu Lys His Gly Phe Asp Glu Trp Phe
145                 150                 155                 160

Gly Ser Pro Asn Cys His Phe Gly Pro Tyr Asp Asn Lys Leu Arg Gly
                165                 170                 175

Gln Ile Pro Val Tyr Arg Asp Trp Glu Met Val Gly Arg Tyr Tyr Glu
            180                 185                 190

Glu Phe Pro Ile Asn Leu Lys Thr Gly Glu Ala Asn Leu Thr Gln Ile
        195                 200                 205

Tyr Leu Gln Glu Ala Leu Asp Phe Ile Lys Arg Gln Ala Arg His His
    210                 215                 220

Pro Phe Phe Leu Ile Trp Leu Val Asp Ala Thr His Leu Pro Val Tyr
225                 230                 235                 240

Ala Ser Lys Pro Phe Leu Gly Thr Ser Gln Arg Gly Arg Tyr Gly Asp
                245                 250                 255

Ala Val Arg Glu Ile Asp Asp Ser Ile Gly Lys Ile Leu Glu Leu Leu
            260                 265                 270

Gln Asp Leu His Val Ala Asp Asn Thr Phe Val Phe Thr Ser Asp
    275                 280                 285

Asn Gly Ala Ala Leu Ile Ser Ala Pro Glu Gln Gly Gly Ser Asn Gly
290                 295                 300

Pro Phe Leu Cys Gly Lys Gln Thr Thr Phe Glu Gly Gly Met Arg Glu
305                 310                 315                 320

Pro Ala Leu Ala Trp Trp Pro Gly His Val Thr Ala Gly Gln Val Ser
                325                 330                 335

His Gln Leu Gly Ser Ile Met Asp Leu Phe Thr Thr Ser Leu Ala Leu
            340                 345                 350

Ala Gly Leu Thr Pro Pro Ser Asp Arg Ala Ile Asp Gly Leu Asn Leu
        355                 360                 365

Leu Pro Thr Leu Leu Gln Gly Arg Leu Met Asp Arg Pro Ile Phe Tyr
    370                 375                 380

Tyr Arg Gly Asp Thr Leu Met Ala Ala Thr Leu Gly Gln His Lys Ala
385                 390                 395                 400

His Phe Trp Thr Trp Thr Asn Ser Trp Glu Asn Phe Arg Gln Gly Ile
                405                 410                 415

Asp Phe Cys Pro Gly Gln Asn Val Ser Gly Val Thr Thr His Asn Leu
            420                 425                 430

Glu Asp His Thr Lys Leu Pro Leu Ile Phe His Leu Gly Arg Asp Pro
        435                 440                 445

Gly Glu Arg Phe Pro Leu Ser Phe Ala Ser Ala Glu Tyr Gln Glu Ala
    450                 455                 460

Leu Ser Arg Ile Thr Ser Val Val Gln Gln His Gln Glu Ala Leu Val
465                 470                 475                 480

Pro Ala Gln Pro Gln Leu Asn Val Cys Asn Trp Ala Val Met Asn Trp
                485                 490                 495

Ala Pro Pro Gly Cys Glu Lys Leu Gly Lys Cys Leu Thr Pro Pro Glu
            500                 505                 510

Ser Ile Pro Lys Lys Cys Leu Trp Ser His
        515                 520

<210> SEQ ID NO 8
<211> LENGTH: 522

<212> TYPE: PRT
<213> ORGANISM: Homo sapiens

<400> SEQUENCE: 8

```
Met Ala Ala Val Val Ala Ala Thr Arg Trp Trp Gln Leu Leu Leu Val
1               5                   10                  15

Leu Ser Ala Ala Gly Met Gly Ala Ser Gly Ala Pro Gln Pro Pro Asn
            20                  25                  30

Ile Leu Leu Leu Leu Met Asp Asp Met Gly Trp Gly Asp Leu Gly Val
        35                  40                  45

Tyr Gly Glu Pro Ser Arg Glu Thr Pro Asn Leu Asp Arg Met Ala Ala
    50                  55                  60

Glu Gly Leu Leu Phe Pro Asn Phe Tyr Ser Ala Asn Pro Leu Cys Ser
65                  70                  75                  80

Pro Ser Arg Ala Ala Leu Leu Thr Gly Arg Leu Pro Ile Arg Asn Gly
                85                  90                  95

Phe Tyr Thr Thr Asn Ala His Ala Arg Asn Ala Tyr Thr Pro Gln Glu
            100                 105                 110

Ile Val Gly Gly Ile Pro Asp Ser Glu Gln Leu Leu Pro Glu Leu Leu
        115                 120                 125

Lys Lys Ala Gly Tyr Val Ser Lys Ile Val Gly Lys Trp His Leu Gly
    130                 135                 140

His Arg Pro Gln Phe His Pro Leu Lys His Gly Phe Asp Glu Trp Phe
145                 150                 155                 160

Gly Ser Pro Asn Cys His Phe Gly Pro Tyr Asp Asn Lys Ala Arg Pro
                165                 170                 175

Asn Ile Pro Val Tyr Arg Asp Trp Glu Met Val Gly Arg Tyr Tyr Glu
            180                 185                 190

Glu Phe Pro Ile Asn Leu Lys Thr Gly Glu Ala Asn Leu Thr Gln Ile
        195                 200                 205

Tyr Leu Gln Glu Ala Leu Asp Phe Ile Lys Arg Gln Ala Arg His His
    210                 215                 220

Pro Phe Phe Leu Ile Trp Ala Val Asp Leu Thr His Ile Pro Val Tyr
225                 230                 235                 240

Ala Ser Lys Pro Phe Leu Gly Thr Ser Gln Arg Gly Arg Tyr Gly Asp
                245                 250                 255

Ala Val Arg Glu Ile Asp Asp Ser Ile Gly Lys Ile Leu Glu Leu Leu
            260                 265                 270

Gln Asp Leu His Val Ala Asp Asn Thr Phe Val Phe Phe Thr Ser Asp
        275                 280                 285

Asn Gly Ala Ala Leu Ile Ser Ala Pro Glu Gln Gly Gly Ser Asn Gly
    290                 295                 300

Pro Phe Leu Cys Gly Lys Gln Thr Thr Phe Glu Gly Gly Met Arg Glu
305                 310                 315                 320

Pro Ala Leu Ala Trp Trp Pro Gly His Val Thr Ala Gly Gln Val Ser
                325                 330                 335

His Gln Leu Gly Ser Ile Met Asp Leu Phe Thr Thr Ser Leu Ala Leu
            340                 345                 350

Ala Gly Leu Thr Pro Pro Ser Asp Arg Ala Ile Asp Gly Leu Asn Leu
        355                 360                 365

Leu Pro Thr Leu Leu Gln Gly Arg Leu Met Asp Arg Pro Ile Phe Tyr
    370                 375                 380

Tyr Arg Gly Asp Thr Leu Met Ala Ala Thr Leu Gly Gln His Lys Ala
385                 390                 395                 400
```

-continued

```
His Phe Trp Thr Trp Thr Asn Ser Trp Glu Asn Phe Arg Gln Gly Ile
                405                 410                 415

Asp Phe Cys Pro Gly Gln Asn Val Ser Gly Val Thr His Asn Leu
            420                 425                 430

Glu Asp His Thr Lys Leu Pro Leu Ile Phe His Leu Gly Arg Asp Pro
        435                 440                 445

Gly Glu Arg Phe Pro Leu Ser Phe Ala Ser Ala Glu Tyr Gln Glu Ala
    450                 455                 460

Leu Ser Arg Ile Thr Ser Val Val Gln Gln His Gln Glu Ala Leu Val
465                 470                 475                 480

Gly Ile Gln Gly Gln Leu Asn Val Cys Asn Trp Ala Val Met Asn Trp
                485                 490                 495

Ala Pro Pro Gly Cys Glu Lys Leu Gly Lys Cys Leu Thr Pro Pro Glu
            500                 505                 510

Ser Ile Pro Lys Lys Cys Leu Trp Ser His
            515                 520

<210> SEQ ID NO 9
<211> LENGTH: 20
<212> TYPE: PRT
<213> ORGANISM: Homo sapiens

<400> SEQUENCE: 9

Pro Asn Cys His Phe Gly Pro Tyr Asp Asn Lys Ala Arg Pro Asn Ile
1               5                   10                  15

Pro Val Tyr Arg
            20

<210> SEQ ID NO 10
<211> LENGTH: 20
<212> TYPE: PRT
<213> ORGANISM: Homo sapiens

<400> SEQUENCE: 10

Phe Phe Leu Tyr Trp Ala Val Asp Ala Thr His Ala Pro Val Tyr Ala
1               5                   10                  15

Ser Lys Pro Phe
            20

<210> SEQ ID NO 11
<211> LENGTH: 20
<212> TYPE: PRT
<213> ORGANISM: Homo sapiens

<400> SEQUENCE: 11

Gln Gln His Gln Glu Ala Leu Val Pro Ala Gln Pro Gln Leu Asn Val
1               5                   10                  15

Thr Asn Trp Ala
            20

<210> SEQ ID NO 12
<211> LENGTH: 15
<212> TYPE: PRT
<213> ORGANISM: Homo sapiens

<400> SEQUENCE: 12

Tyr Gly Glu Pro Ser Arg Glu Thr Pro Asn Leu Asp Arg Met Ala
1               5                   10                  15
```

```
<210> SEQ ID NO 13
<211> LENGTH: 15
<212> TYPE: PRT
<213> ORGANISM: Homo sapiens

<400> SEQUENCE: 13

Ala His Ala Arg Asn Ala Tyr Thr Pro Gln Glu Ile Val Gly Gly
1               5                   10                  15

<210> SEQ ID NO 14
<211> LENGTH: 15
<212> TYPE: PRT
<213> ORGANISM: Homo sapiens

<400> SEQUENCE: 14

Ala Arg Pro Asn Ile Pro Val Tyr Arg Asp Trp Glu Met Val Gly
1               5                   10                  15

<210> SEQ ID NO 15
<211> LENGTH: 15
<212> TYPE: PRT
<213> ORGANISM: Homo sapiens

<400> SEQUENCE: 15

Ser Leu Ala Leu Ala Gly Leu Thr Pro Pro Ser Asp Arg Ala Ile
1               5                   10                  15

<210> SEQ ID NO 16
<211> LENGTH: 15
<212> TYPE: PRT
<213> ORGANISM: Homo sapiens

<400> SEQUENCE: 16

Gly Trp Gly Asp Leu Gly Val Tyr Gly Glu Pro Ser Arg Glu Thr
1               5                   10                  15

<210> SEQ ID NO 17
<211> LENGTH: 15
<212> TYPE: PRT
<213> ORGANISM: Homo sapiens

<400> SEQUENCE: 17

Asn Ala His Ala Arg Asn Ala Tyr Thr Pro Gln Glu Ile Val Gly
1               5                   10                  15

<210> SEQ ID NO 18
<211> LENGTH: 15
<212> TYPE: PRT
<213> ORGANISM: Homo sapiens

<400> SEQUENCE: 18

Ser Lys Pro Phe Leu Gly Thr Ser Gln Arg Gly Arg Tyr Gly Asp
1               5                   10                  15

<210> SEQ ID NO 19
<211> LENGTH: 15
<212> TYPE: PRT
<213> ORGANISM: Homo sapiens

<400> SEQUENCE: 19

Asp Ala Thr His Ala Pro Val Tyr Ala Ser Lys Pro Phe Leu Gly
1               5                   10                  15

<210> SEQ ID NO 20
<211> LENGTH: 15
```

```
<212> TYPE: PRT
<213> ORGANISM: Homo sapiens

<400> SEQUENCE: 20

Glu Ala Leu Ser Arg Ile Thr Ser Val Val Gln Gln His Gln Glu
1               5                   10                  15

<210> SEQ ID NO 21
<211> LENGTH: 15
<212> TYPE: PRT
<213> ORGANISM: Homo sapiens

<400> SEQUENCE: 21

Tyr Ser Ala Asn Pro Leu Cys Ser Pro Ser Arg Ala Ala Leu Leu
1               5                   10                  15

<210> SEQ ID NO 22
<211> LENGTH: 15
<212> TYPE: PRT
<213> ORGANISM: Homo sapiens

<400> SEQUENCE: 22

Glu Lys Leu Gly Lys Cys Leu Thr Pro Pro Glu Ser Ile Pro Lys
1               5                   10                  15

<210> SEQ ID NO 23
<211> LENGTH: 15
<212> TYPE: PRT
<213> ORGANISM: Homo sapiens

<400> SEQUENCE: 23

Gln Glu Ala Leu Ser Arg Ile Thr Ser Val Val Gln Gln His Gln
1               5                   10                  15

<210> SEQ ID NO 24
<211> LENGTH: 9
<212> TYPE: PRT
<213> ORGANISM: Homo sapiens

<400> SEQUENCE: 24

Leu Thr Pro Pro Ser Asp Arg Ala Ile
1               5

<210> SEQ ID NO 25
<211> LENGTH: 9
<212> TYPE: PRT
<213> ORGANISM: Homo sapiens

<400> SEQUENCE: 25

Asn Pro Leu Cys Ser Pro Ser Arg Ala
1               5

<210> SEQ ID NO 26
<211> LENGTH: 9
<212> TYPE: PRT
<213> ORGANISM: Homo sapiens

<400> SEQUENCE: 26

Gln Glu Ala Leu Ser Arg Ile Thr Ser
1               5

<210> SEQ ID NO 27
<211> LENGTH: 9
<212> TYPE: PRT
<213> ORGANISM: Homo sapiens
```

```
<400> SEQUENCE: 27

His Gln Leu Gly Ser Ile Met Asp Leu
1               5

<210> SEQ ID NO 28
<211> LENGTH: 9
<212> TYPE: PRT
<213> ORGANISM: Homo sapiens

<400> SEQUENCE: 28

Glu Ile Asp Asp Ser Ile Gly Lys Ile
1               5

<210> SEQ ID NO 29
<211> LENGTH: 9
<212> TYPE: PRT
<213> ORGANISM: Homo sapiens

<400> SEQUENCE: 29

Ser Arg Ile Thr Ser Val Val Gln Gln
1               5

<210> SEQ ID NO 30
<211> LENGTH: 9
<212> TYPE: PRT
<213> ORGANISM: Homo sapiens

<400> SEQUENCE: 30

Leu Ser Phe Ala Ser Ala Glu Tyr Gln
1               5

<210> SEQ ID NO 31
<211> LENGTH: 9
<212> TYPE: PRT
<213> ORGANISM: Homo sapiens

<400> SEQUENCE: 31

Ala Gly Tyr Val Ser Lys Ile Val Gly
1               5

<210> SEQ ID NO 32
<211> LENGTH: 9
<212> TYPE: PRT
<213> ORGANISM: Homo sapiens

<400> SEQUENCE: 32

Thr Trp Thr Asn Ser Trp Glu Asn Phe
1               5

<210> SEQ ID NO 33
<211> LENGTH: 9
<212> TYPE: PRT
<213> ORGANISM: Homo sapiens

<400> SEQUENCE: 33

Pro Ser Arg Glu Thr Pro Asn Leu Asp
1               5

<210> SEQ ID NO 34
<211> LENGTH: 9
<212> TYPE: PRT
<213> ORGANISM: Homo sapiens

<400> SEQUENCE: 34
```

```
Tyr Arg Gly Asp Thr Leu Met Ala Ala
1               5
```

<210> SEQ ID NO 35
<211> LENGTH: 9
<212> TYPE: PRT
<213> ORGANISM: Homo sapiens

<400> SEQUENCE: 35

```
Cys Gly Lys Gln Thr Thr Phe Glu Gly
1               5
```

<210> SEQ ID NO 36
<211> LENGTH: 9
<212> TYPE: PRT
<213> ORGANISM: Homo sapiens

<400> SEQUENCE: 36

```
Gly Lys Cys Leu Thr Pro Pro Glu Ser
1               5
```

<210> SEQ ID NO 37
<211> LENGTH: 9
<212> TYPE: PRT
<213> ORGANISM: Homo sapiens

<400> SEQUENCE: 37

```
Leu Ser Arg Ile Thr Ser Val Val Gln
1               5
```

<210> SEQ ID NO 38
<211> LENGTH: 9
<212> TYPE: PRT
<213> ORGANISM: Homo sapiens

<400> SEQUENCE: 38

```
His Ala Pro Val Tyr Ala Ser Lys Pro
1               5
```

<210> SEQ ID NO 39
<211> LENGTH: 9
<212> TYPE: PRT
<213> ORGANISM: Homo sapiens

<400> SEQUENCE: 39

```
Lys Lys Ala Gly Tyr Val Ser Lys Ile
1               5
```

<210> SEQ ID NO 40
<211> LENGTH: 9
<212> TYPE: PRT
<213> ORGANISM: Homo sapiens

<400> SEQUENCE: 40

```
Arg Asn Gly Phe Tyr Thr Thr Asn Ala
1               5
```

```
<210> SEQ ID NO 41
<211> LENGTH: 9
<212> TYPE: PRT
<213> ORGANISM: Homo sapiens

<400> SEQUENCE: 41

His Phe Gly Pro Tyr Asp Asn Lys Ala
1               5
```

REDUCED IMMUNOGENIC PROTEINS FOR LYSOSOMAL STORAGE DISORDERS

CROSS REFERENCE TO RELATED APPLICATIONS

This application is a divisional application of U.S. Patent Publication No. 2018/0073000, filed Jan. 20, 2017, which claims priority to U.S. provisional application 62/281,611, filed Jan. 21, 2016, each of which is hereby incorporated by reference in its entirety.

INCORPORATION OF SEQUENCE LISTING

A paper copy of the Sequence Listing and a computer readable form of the Sequence Listing containing the file named "SLU 15-006_ST25.txt", which is 42,225 bytes in size (as measured in MICROSOFT WINDOWS® EXPLORER), are provided herein and are herein incorporated by reference. This Sequence Listing consists of SEQ ID NOs:1-41.

FIELD OF THE INVENTION

The invention relates to methods and compositions used for enzyme replacement therapy in the treatment of subjects with lysosomal storages disorders. More specifically, the invention relates variants of N-acetylgalactosamine-6-sulfatase with reduced immunogenicity to be used in subjects suffering from Mucopolysaccharidosis type IVA.

BACKGROUND

Mucopolysaccharidosis IVA (Morquio A disease, MPS IVA) is a lysosomal storage disease in which there is a deficiency of the protein N-acetylgalactosamine-6-sulfate sulfatase (GALNS).[1] It is a rare autosomal recessive disorder that affects about 1 in 250,000 live births.[2] The accumulation of chondroitin-6-sulfate (C6S) and keratan sulfate (KS) results in systemic skeletal chondrodysplasia.[1,3] Additional clinical manifestations of Morquio A disease include elevated blood and urine C6S and KS levels, hypoplasia of the odontoid process, pectus carinatum, marked short stature, knock knees, kyphoscoliosis, and corneal clouding.[1]

In 2014, the FDA approved enzyme replacement therapy (ERT) for Morquio A disease based on limited improvement in the 6 minute walk test (Hendriksz, C. J., (2014) J Inherit Metab Dis 37(6):979-90). Enzyme replacement therapy replaces the deficient enzyme in an affected patient through intravenous infusion.[4] This prevents the progression of MPS IVA by increasing the concentration of GALNS in cells.[4] However, it does not affect the causal mechanism of the defect. One challenge that is encountered is that the replaced enzyme is seen as foreign to the body and provokes an immune response. The immunogenic response develops in the patient against the replacement enzyme including hypersensitivity reactions, neutralizing antibodies, and modified enzyme targeting or turnover,[6] all of which significantly decreases the efficacy of treatment. An immune response in human and animal models is developed in all available enzyme replacement therapies for lysosomal storage diseases, including the FDA approved ERTs. Preclinical trials of enzyme replacement therapy (ERT) in Mucopolysaccharidosis IVA (Morquio A disease, MPS IVA) has been shown to successfully treat the disease, but the immune response that accompanies this treatment significantly decreases efficacy. The patient may not develop tolerance until 2 to 3 years after their initial dose of ERT which results in 2 to 3 years of substandard therapy at an annual cost of ERT ranging from $200,000 to $500,000 per patient. The current approach is to counteract the immune response with immunosuppressive protocols.[6] However, this leaves the patient susceptible to infection, may result in drug-drug interactions, increases cost of therapy, in addition to other side effects. A number of factors including the nature of the infused protein, genetic background of the patient, route of enzyme administration, frequency and dose of treatment, as well as structural differences between the infused and the defective protein and environmental factors, may all contribute to this immune response which occurs during ERT in LSDs, and presents one of the major complications of this treatment.

Morquio A disease (MPS IVA), which involves a deficiency of the N-acetylgalactosamine-6-sulfate sulfatase (GALNS), is particularly affected. To alleviate immunoreactions associated with ERT for Morquio, the Inventors have bioengineered variants of the GALNS protein with reduced immunogenicity and without a significant loss of biological activity. Using the FASTA format of the GALNS sequences and computational programs, the Inventors have evaluated predictions of the immunogenicity, post-translational modifications, physic chemical properties, and molecular docking, thus allowing them to rapidly narrow 324 potential modified GALNS sequences to 7 modified GALNS sequences predicted to contain properties most similar to the original GALNS protein. In vitro studies were performed by transfection of HEK293 cells with cDNA of the seven sequences. Results indicate that three out of seven mutated GALNS sequences retained 80% or more enzyme activity relative to the wild type GALNS in vitro. Production of the modified GALNS sequences in COS-7 cells co-transfected with SUMF1 resulted in an additional increase in activity.

The development of a less immunogenic GALNS protein provides improved efficacy of ERT for treatment for MPS IV, and will alleviate the need for immunosuppressive protocols of ERT.

SUMMARY OF THE INVENTION

In one aspect, the present disclosure is directed to a modified N-acetylgalactosamine-6-sulfate sulfatase (GALNS) with reduced immunogenic properties and at least 60 percent GALNS activity.

In one aspect, the present disclosure is directed to a modified N-acetylgalactosamine-6-sulfate sulfatase (GALNS) produced by a method comprising: transfecting a cell with a nucleic acid encoding the modified N-acetylgalactosamine-6-sulfate sulfatase (GALNS); and culturing the cell under conditions wherein the cell produces the modified GALNS.

DESCRIPTION OF THE FIGURES

The application file contains at least one figure executed in color. Copies of this patent application publication with color photographs will be provided by the Office upon request and payment of the necessary fee.

DETAILED DESCRIPTION OF THE INVENTION

The Inventors have previously disclosed methods of using bioinformatic tools and in vivo and in vitro immune reactivity assays to identify immunodominant peptides within enzymes administered for enzyme replacement therapy (ERT), including N-acetylgalactosamine-6-sulfatase (GALNS), which is administered for treatment of MPS IVA (see U.S. patent application Ser. No. 13/760,907, incorporated herein by reference in its entirely). The Inventors have shown that immunodominant peptides within GALNS may be used to induce immune tolerance in subject prior to receiving GALNS for ERT. The inventors disclose herein, genetically engineered variants of GALNS, in which these immunodominant peptide regions within GALNS have been modified to present GALNS enzymes with reduced immunogenicity and without an effective reduction in enzyme activity. The inventors believe that this method may also be applied to other enzymes used in ERT, practically those used to treat lysosomal storage disorders (LSDs).

Identification of Immunodominant Peptides and Evaluation of Modifications

The inventors have identified immunodominant peptides of GALNS using bioinformatics tools in combination with target enzyme deficient animals, and in vitro and in vivo humoral and cellular assays for immune response indicators, as disclosed in U.S. patent application Ser. No. 13/760,907 (published as U.S. Patent Pub. No. 2013/0202633).

More specifically, the initial identification of potential immunodominant peptides, was done using bioinformatic tools, RANKPEP (Reche et al. (2002) Human Immunology, 63: 701-709.; Reche et al. (2004) Immunogenetics, 56:405-419; Reche and Reinherz (2007) Methods Mol Biol., 409: 185-200) and Immune Epitope Data Base (Vita et. al., (2010) Nucleic Acids Res. 2010; 38:D854-62). GALNS immunogenicity and prediction of B-cell epitopes were evaluated by the Immune Epitope Data Base (IEDB) analysis resource. The algorithm is based on the predictions of surface accessibility and flexibility of the molecule, and the presence of β-turns and linear epitopes (Zhang et al. (2008) (IEDB-AR). Nucleic Acids Res. 2008: p. W513-8). MHC-II epitopes (H2-IAb) were predicted by IEDB and RANKPEP. Ten peptides were selected by the best scores of $IC_{50}$ nM (concentration of peptide that inhibits binding of a standard peptide by 50%) and binding potential, respectively (Kim, et al. (2011) J. Immunol. Methods, 374(1-2): p. 62-9).

Figures 1A, 1B:
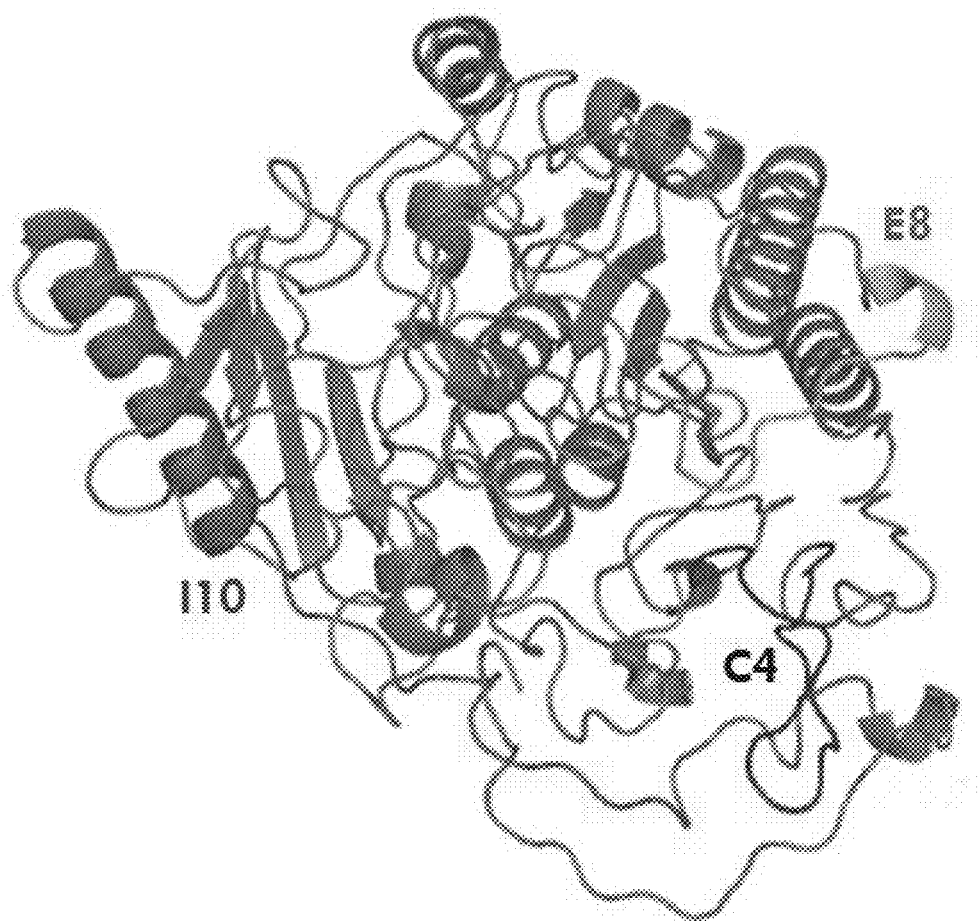
FIGS. 1A and 1B Illustrate the locations of immunodominant peptide regions C4, E8, and I10 in 3D structure of GALNS (FIG. 1A) and GALNS immunodominant epitope sequences: C4 (SEQ ID NO:9), E8 (SEQ ID NO:10), I10 (SEQ ID NO:11) (FIG. 1B).

Of 10 peptides identified by bioinformatics techniques, 3 indicated an increased immunodominant response relative to the 7 remaining peptides, and compared to the intact enzyme (see FIG. 1). This selection was done using immunizing enzyme deficient MKC mice (see U.S. patent application Ser. No. 13/760,907, published as U.S. Patent Pub. No. 2013/0202633). The Inventors chose three immunodominant peptide regions, designated C4, E8, and I10, within the GALNS protein as targets for modification to produce GALNS enzymes with reduced immunogenicity.

The Inventors reasoned that reduced immunogenicity of GALNS may be accomplished by substituting certain amino acid residues within these immunodominant regions. The inventors also reasoned that the tertiary structure of the GALNS protein was an essential consideration when bioengineering GALNS variants, because protein miss-folding is known to be the most common cause of enzyme deficiency in Morquio A disease.[2]

GALNS is a homodimeric glycoprotein with 3 domains in each monomer including an N-terminal domain with the active site, a second domain with antiparallel n-strands, and a C-terminal meander.[2] Each monomer also contains 3 disulfide bonds, 1 unpaired cysteine, many phosphorylation sites, and 2 N-glycosylation sites at Asn204 and Asn423[2]. The GALNS active site contains a calcium ligand bound to 4 residues (D39, D40, D288, N289) and to the catalytic nucleophile DHA79[2]. The N acetylgalactosamine (GalNac) substrate binds to the active site at 3 residues (Y108, H236, K310) and the catalytic nucleophile DHA792. GalNac is a subunit of the dimer chondroitin-6-sulfate, which is comprised of GalNac and glucosamine,[2] Keratan sulfate is a dimer comprised of galactosamine and N-acetylglucosamine.[2]

When making amino acid substitutions within the immunodominant regions, the Inventors considered the following: (1) amino acid substitutions should be made within the same polarity groups, (2) changes to amino acids with significantly different structures compared to the original sequence should be avoiding, by way of example cysteine was not changed because of its potential to form unique sulfide bonding, and (3) changes to amino acids that would create mutations known to be involved in Morquio A disease were also avoided.

Figure 2A:
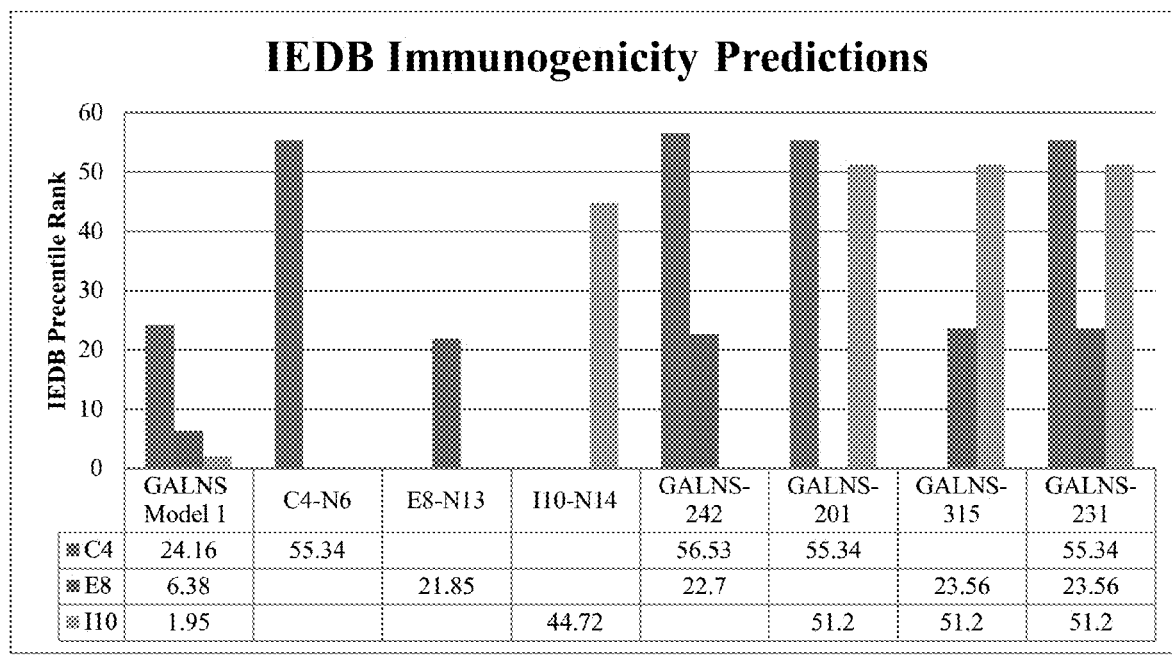
FIGS. 2A and 2B Example of IEDB and RANKPEP output. Modified sequences showed a decreased immunogenicity when compared to the wild type GALNS in IEDB (FIG. 2A) and RANKPEP (FIG. 2B). Higher percentile rank values from IEDB indicate lower immunogenicity. Lower score values from RANKPEP indicate lower immunogenicity.
Figure 2B:
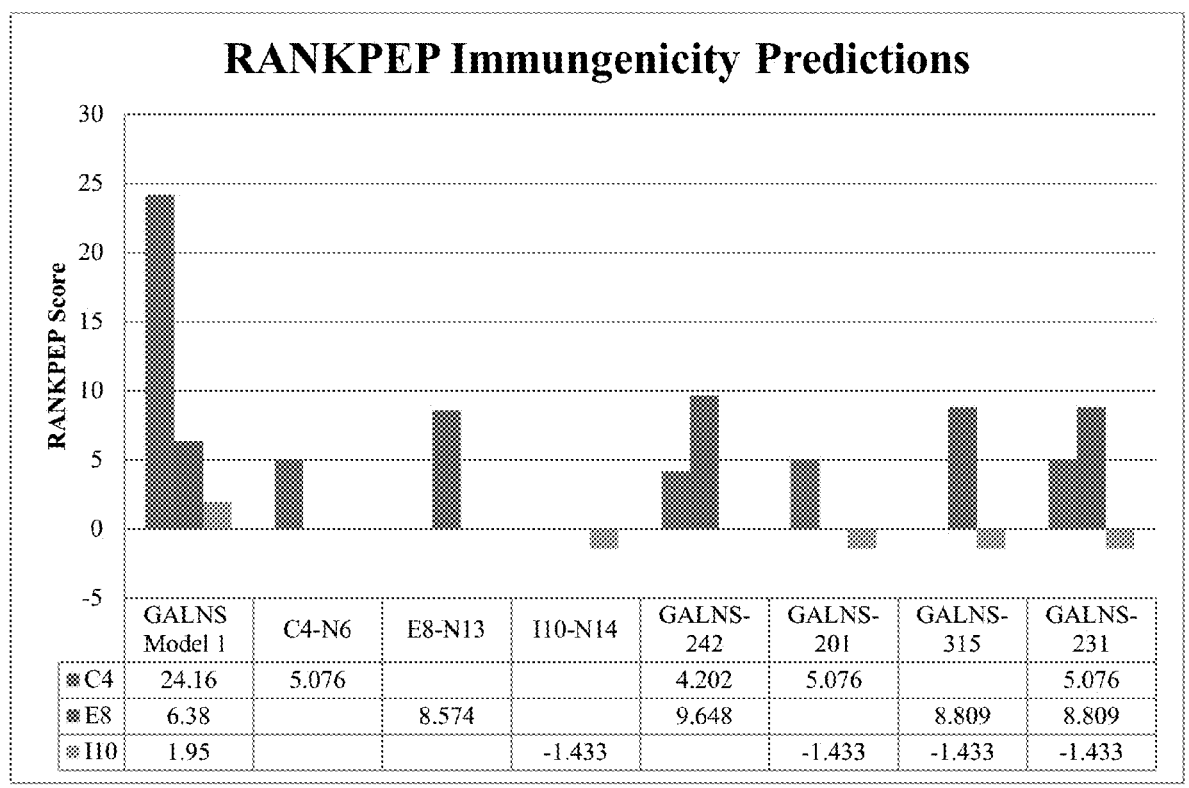
Figure 3A:
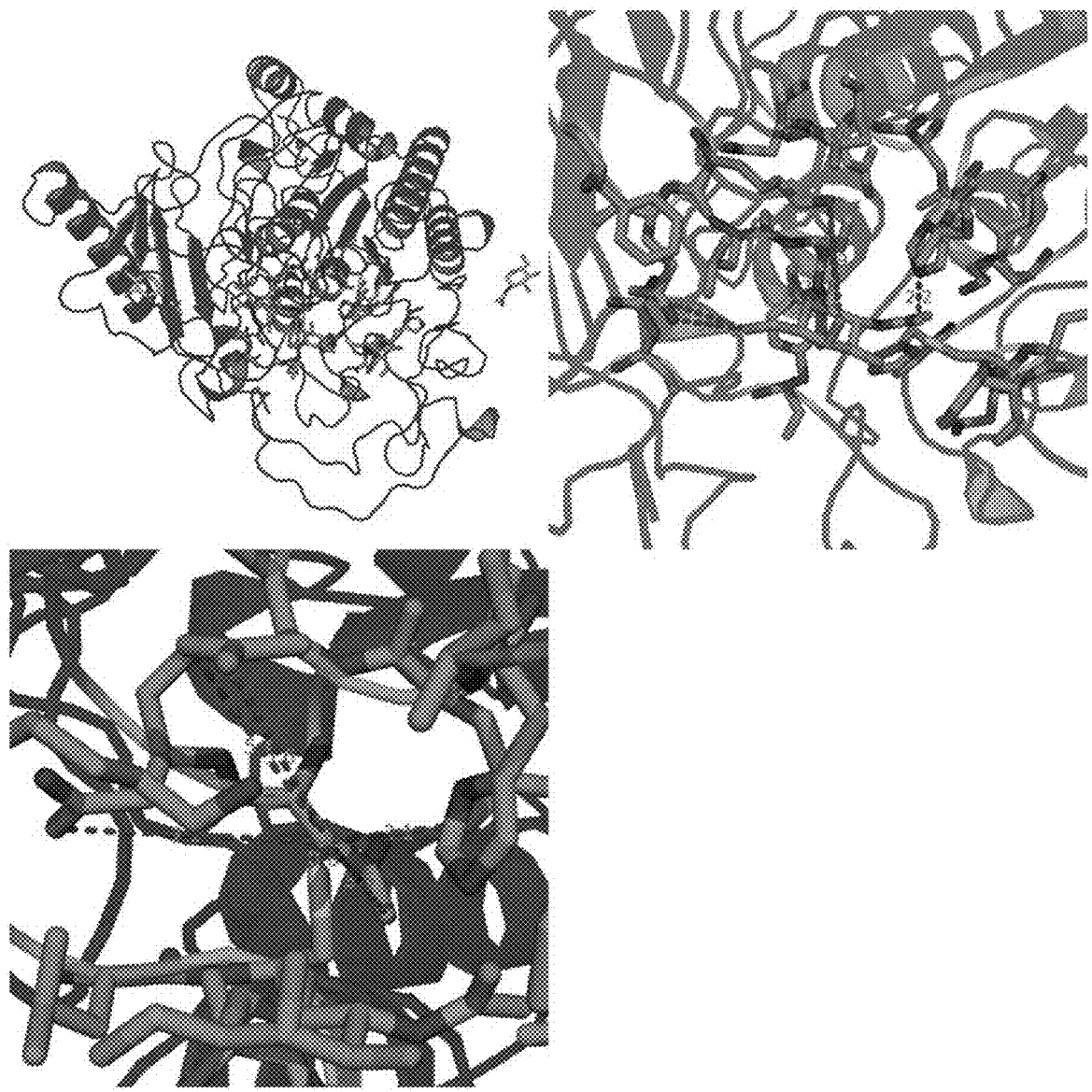
FIG. 3A Molecular docking visualization. The original GALNS Model 1 3D protein structure is depicted in blue. The N-Acetyl-D-Galactosamine (NGA) ligand (orange) binding site is depicted in red with the active site bonds shown in red labeled with their measured distances in angstroms. The calcium (orange asterisk) binding site is depicted in orange with the active site bonds shown in red labeled with their measured distances in angstroms.
Figure 3B:
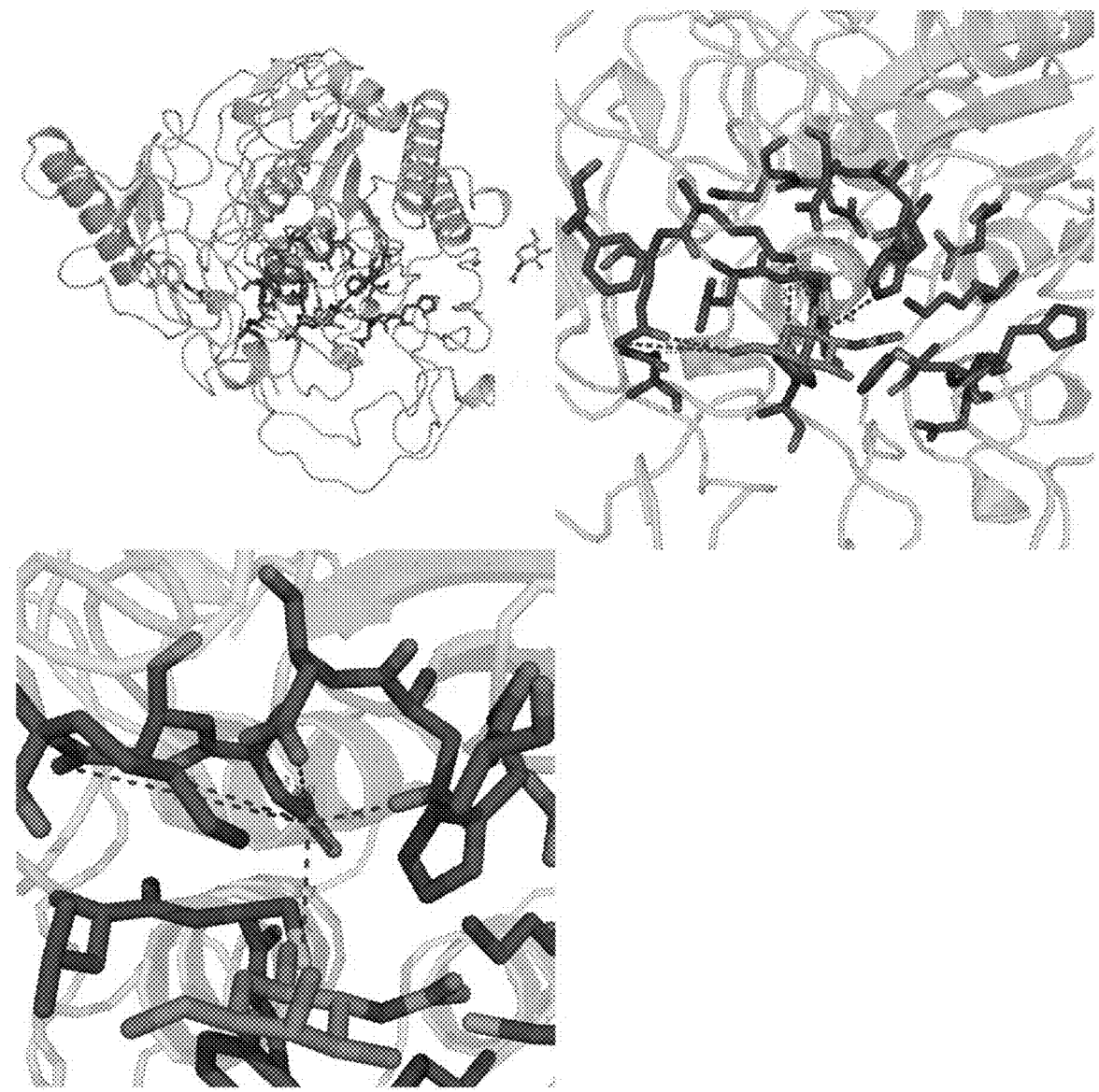
FIG. 3B Molecular docking visualization of modified peptide C4-N6.
Figure 3C:
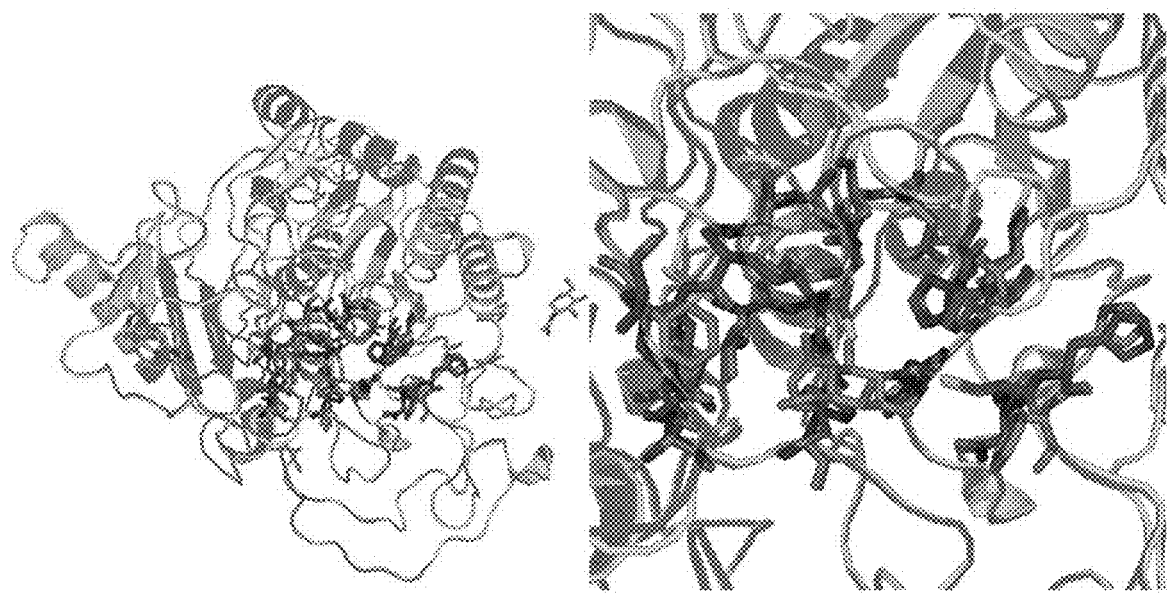
FIG. 3C Molecular docking visualization of modified peptide C4-N6 superimposed onto GALNS.
Figure 3D:
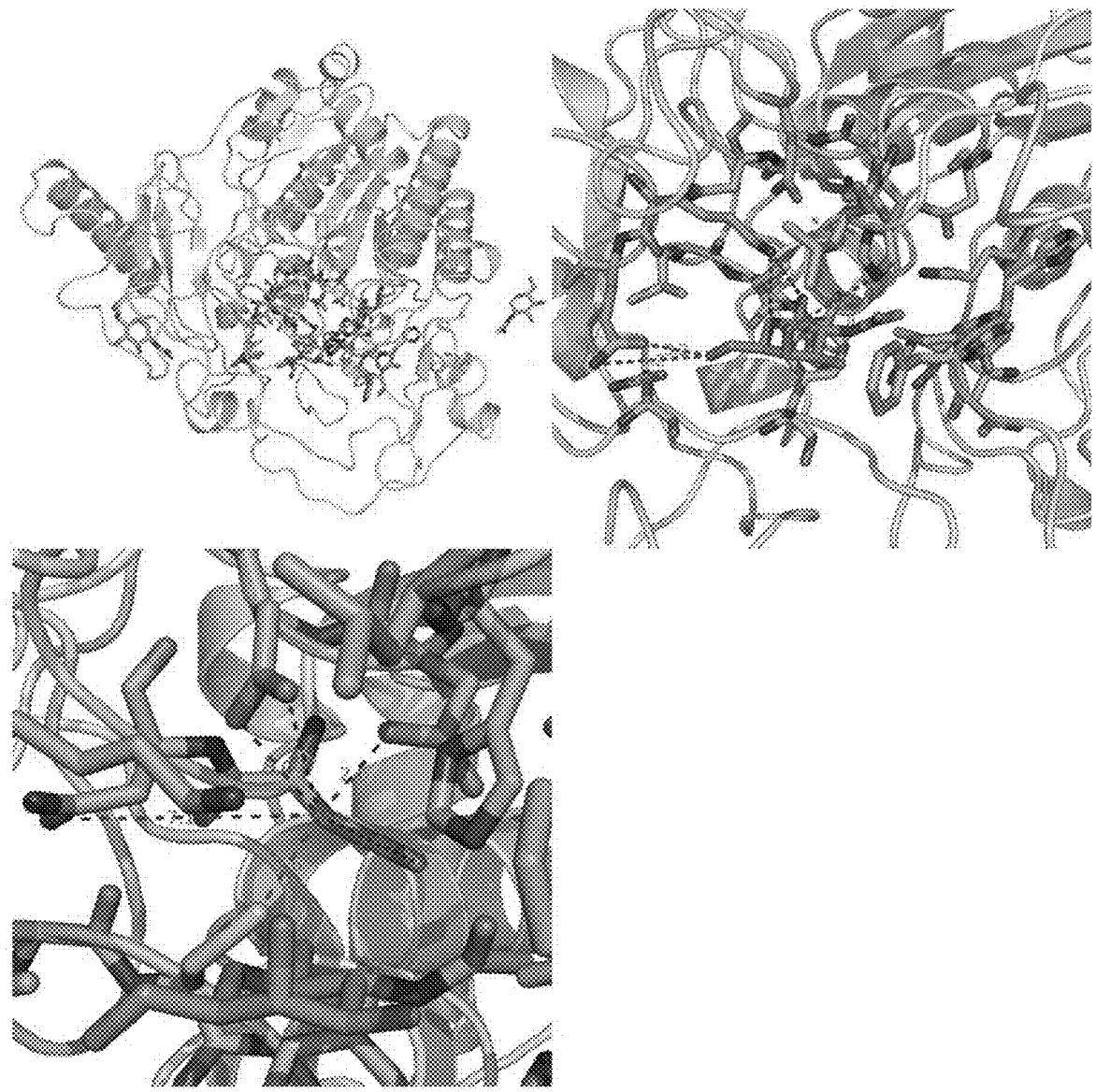
FIG. 3D Molecular docking visualization of modified peptide E8-N13.
Figure 3E:
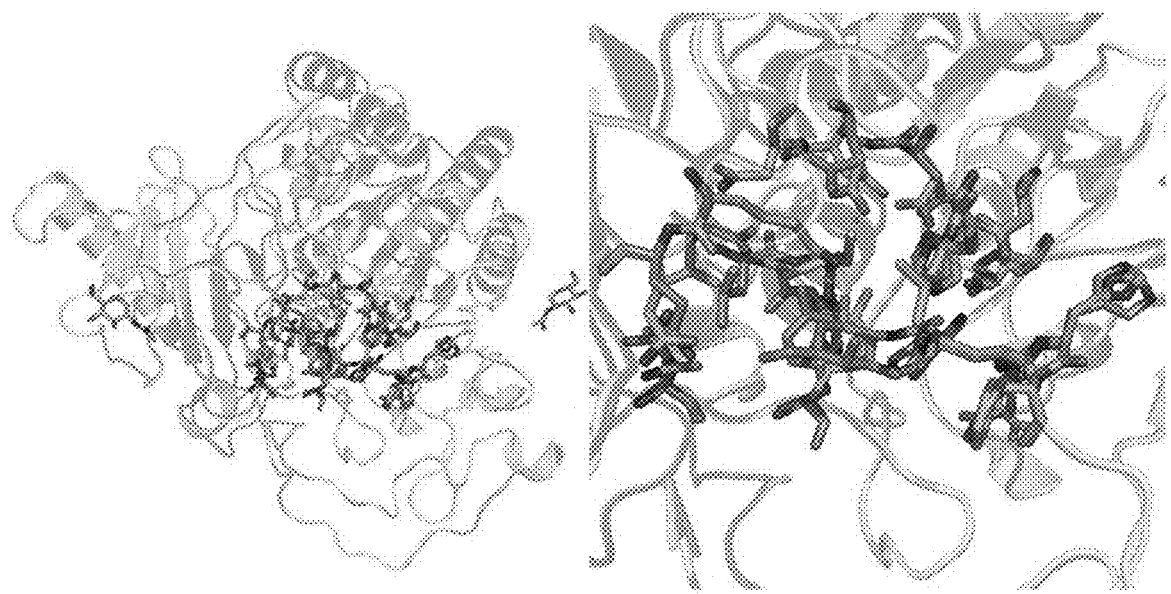
FIG. 3E Molecular docking visualization of modified peptide E8-N13 superimposed onto GALNS Model 1.
Figure 3F:
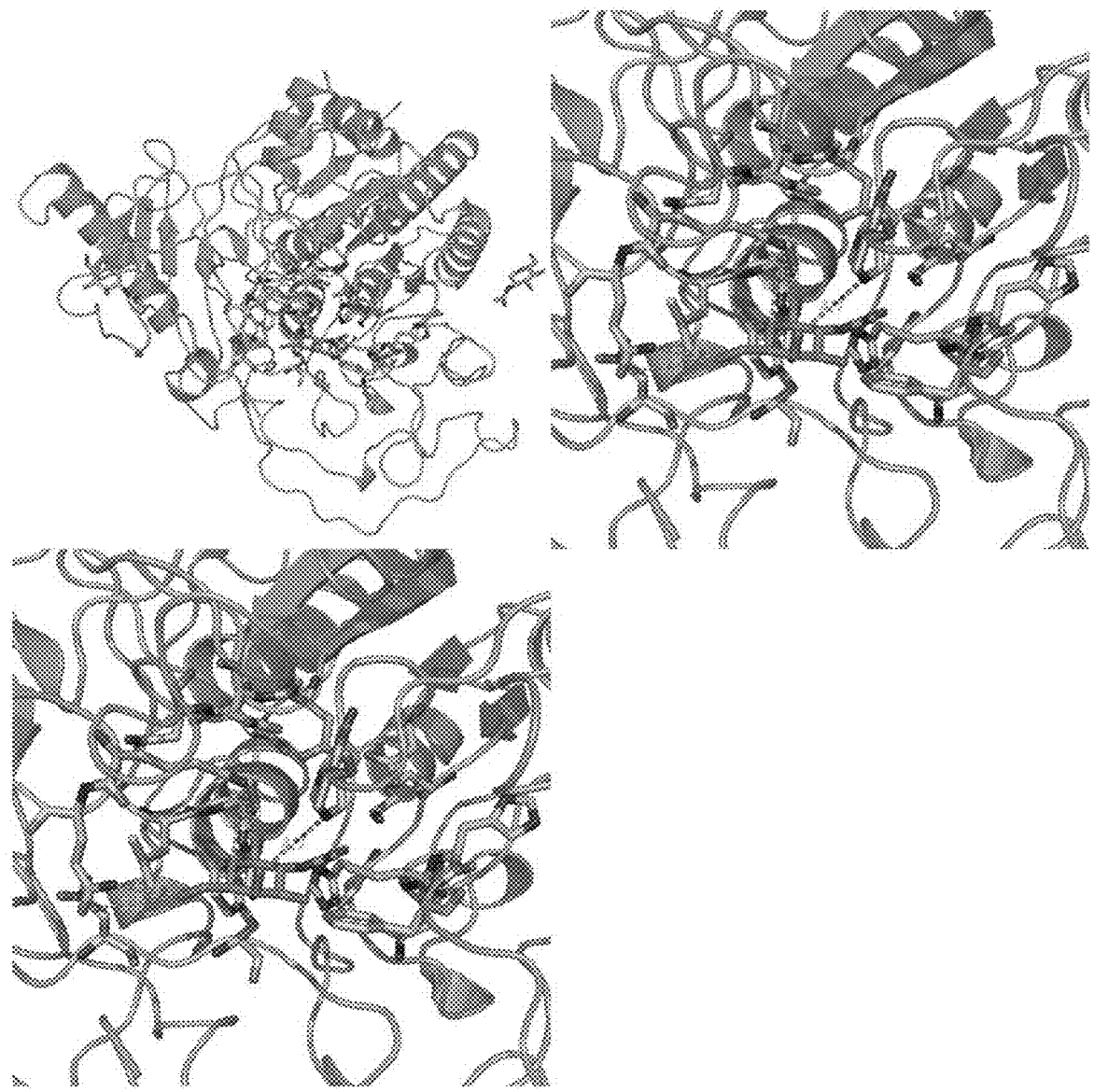
FIG. 3F Molecular docking visualization of modified peptide I10-N14.
Figure 3G:
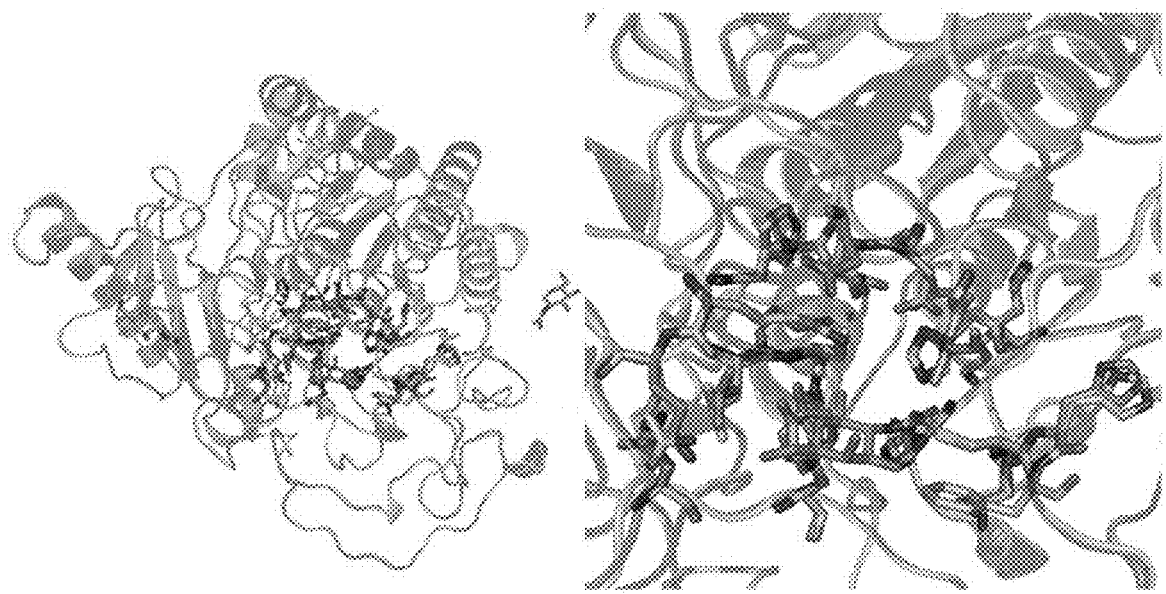
FIG. 3G Molecular docking visualization of modified peptide I10-N14 superimposed onto GALNS.
Figure 3H:
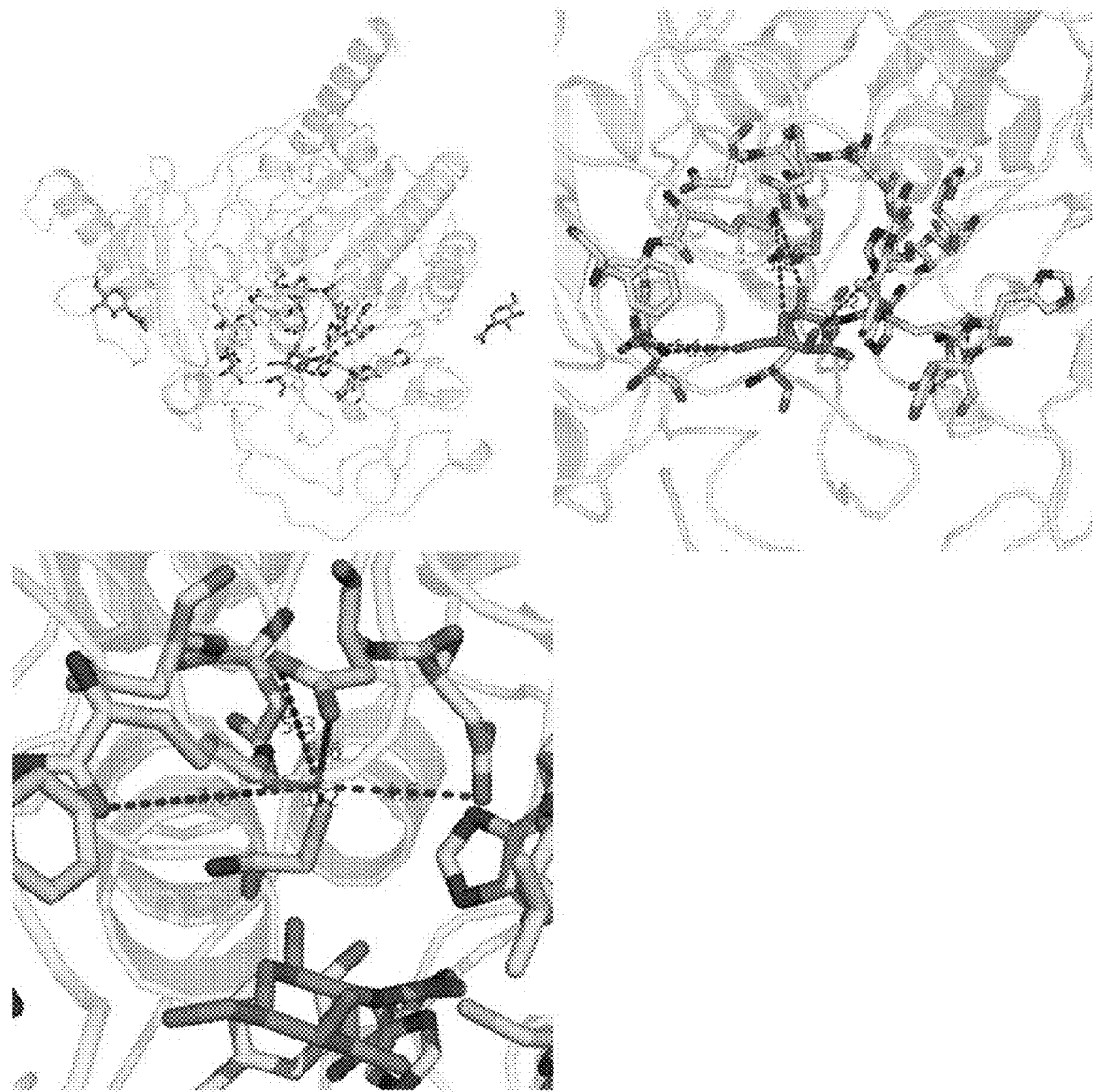
FIG. 3H Molecular docking visualization of modified peptide GALNS-242.
Figure 3I:
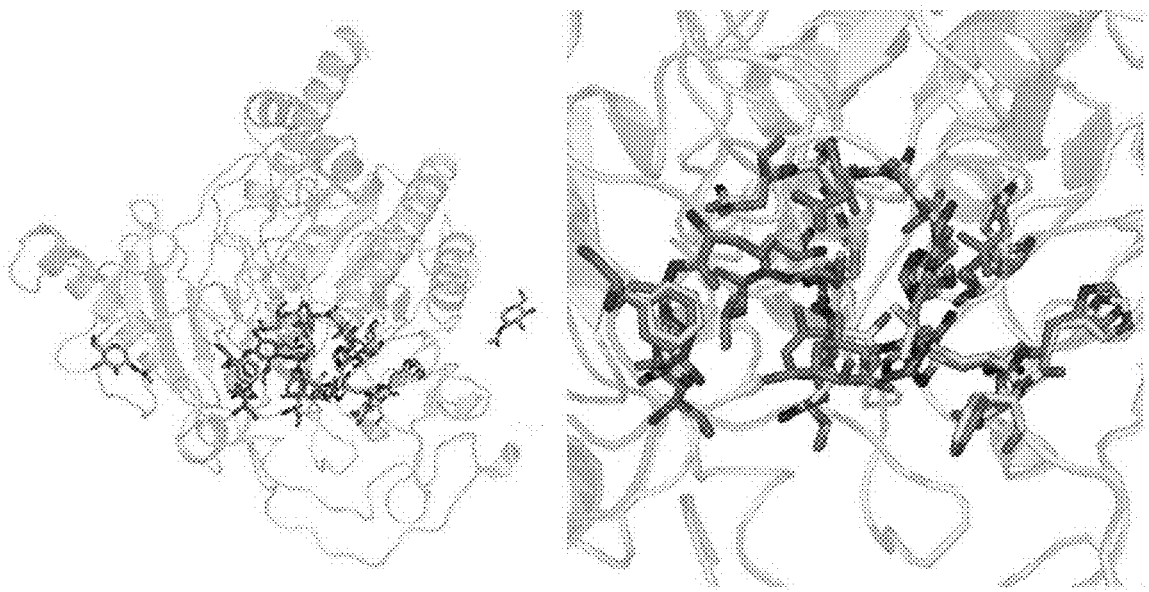
FIG. 3I Molecular docking visualization of modified peptide GALNS-242 superimposed onto GALNS.
Figure 3J:
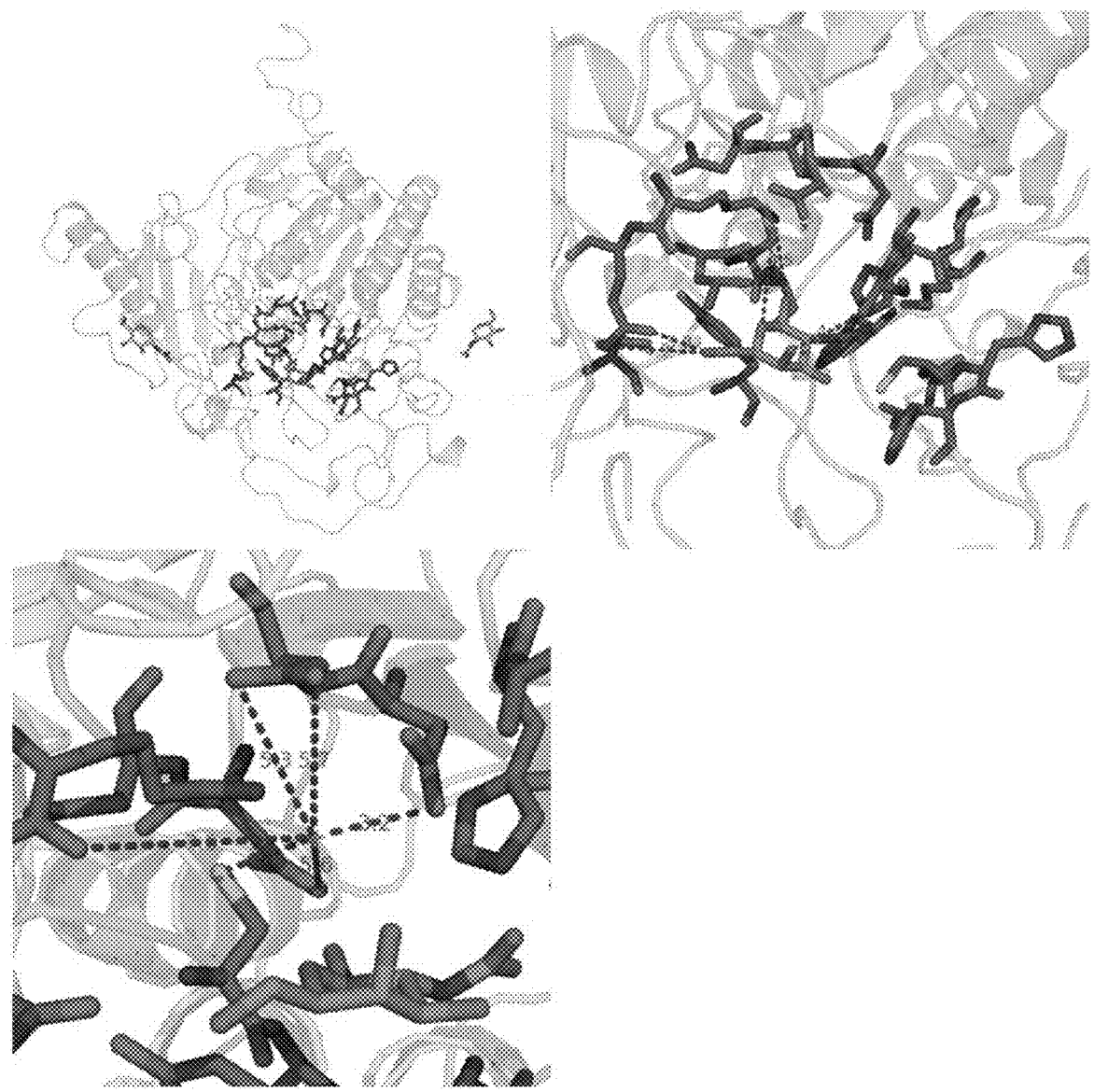
FIG. 3J Molecular docking visualization of modified peptide GALNS-201.
Figure 3K:
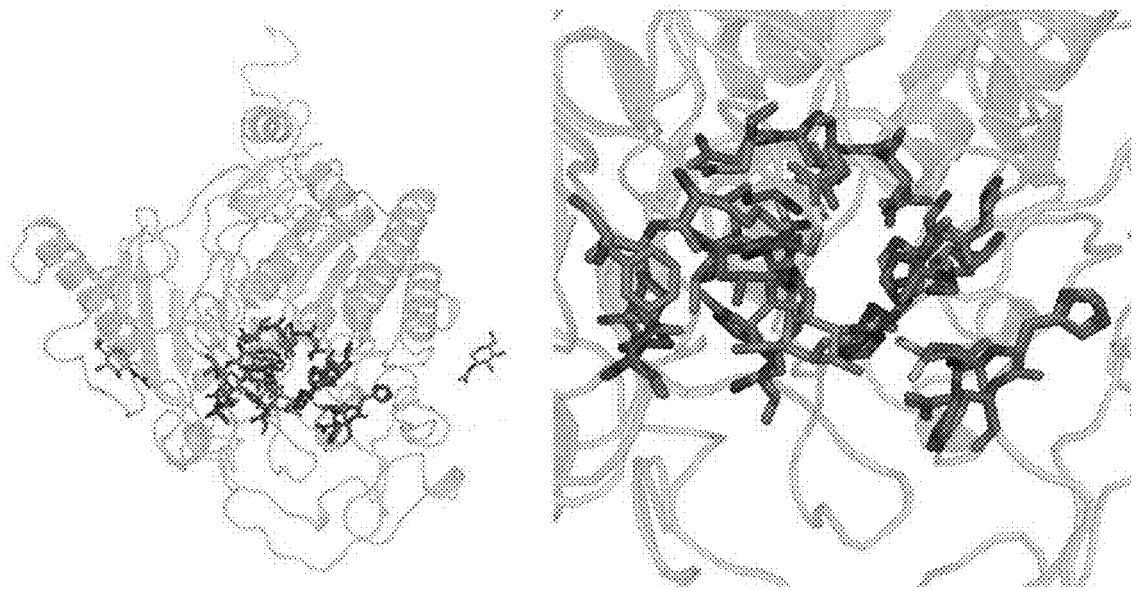
FIG. 3K Molecular docking visualization of modified peptide GALNS-201 superimposed onto GALNS.
Figure 3L:
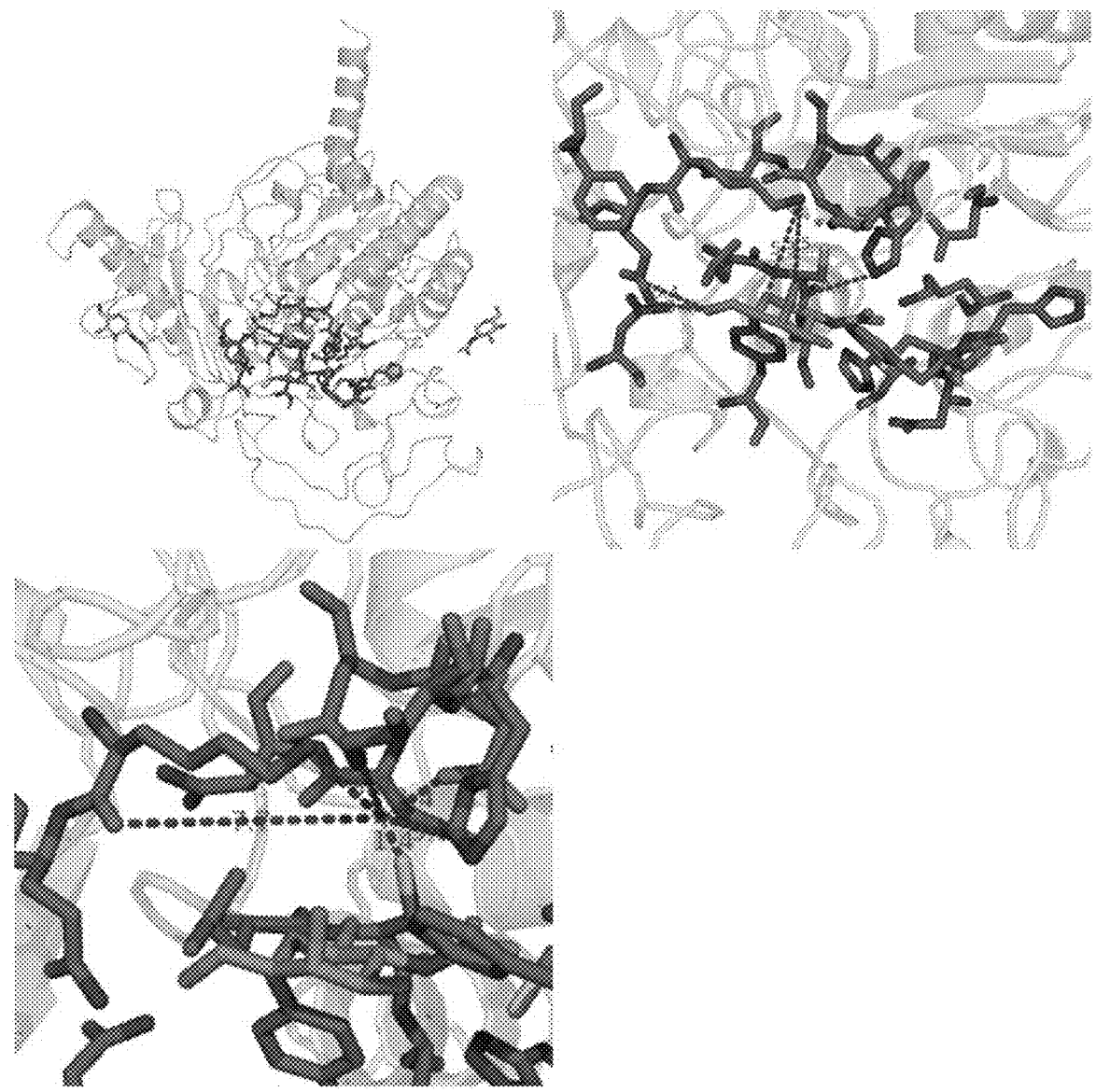
FIG. 3L Molecular docking visualization of modified peptide GALNS-315.
Figure 3M:
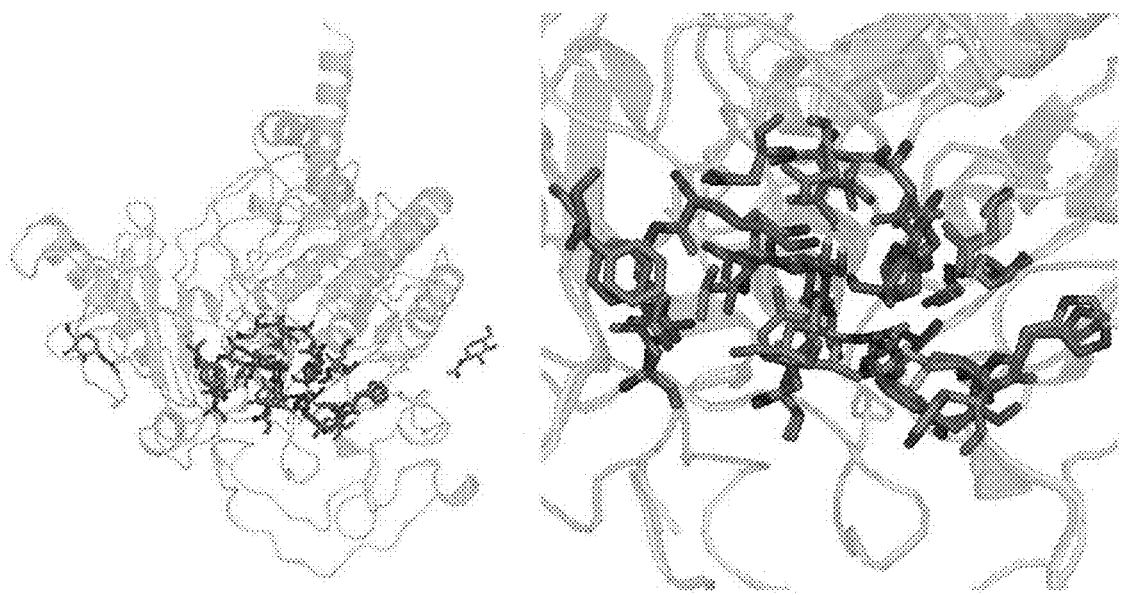
FIG. 3M Molecular docking visualization of modified peptide GALNS-315 superimposed onto GALNS.
Figure 3N:
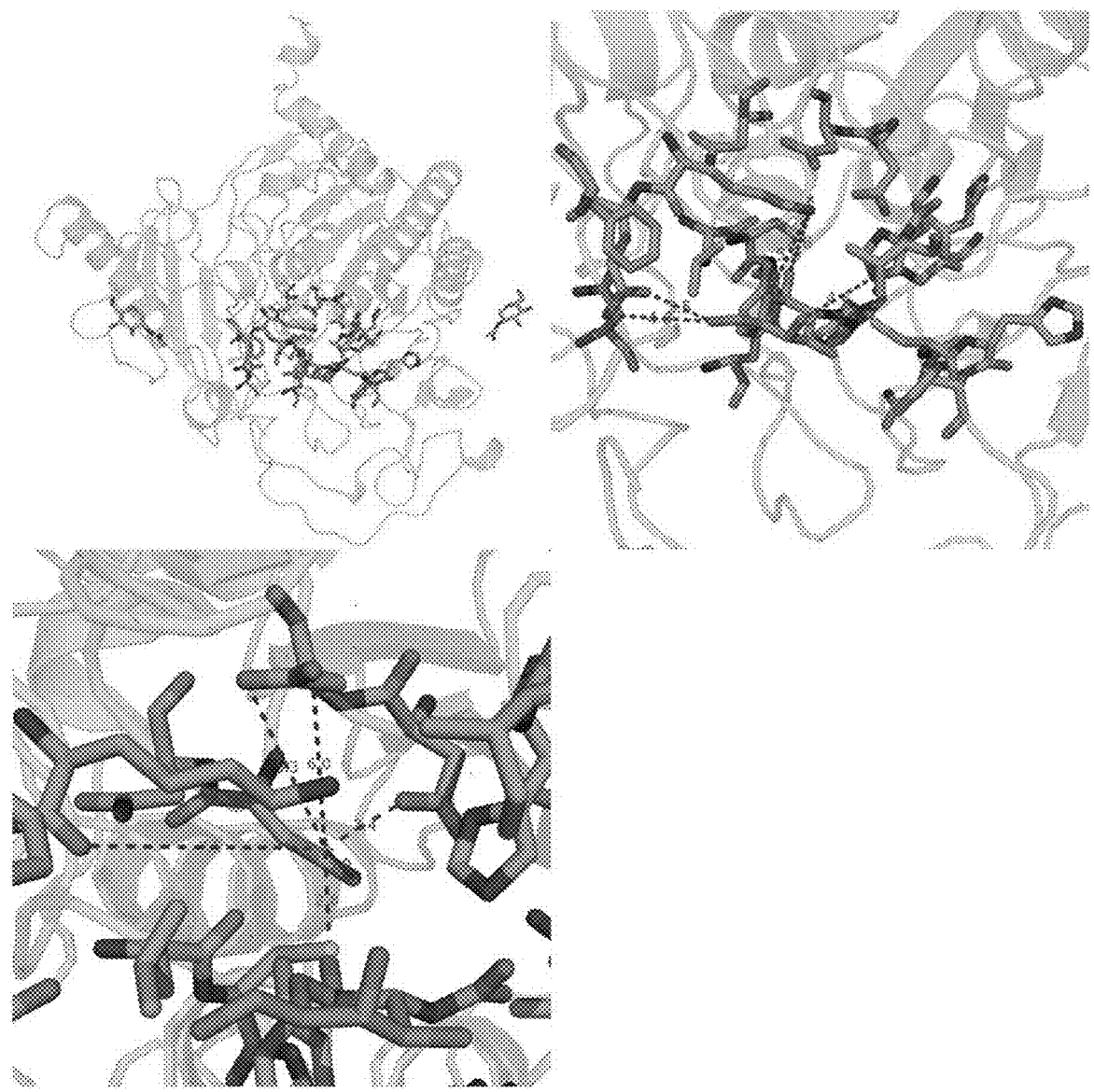
FIG. 3N Molecular docking visualization of modified peptide GALNS-231.
Figure 3O:
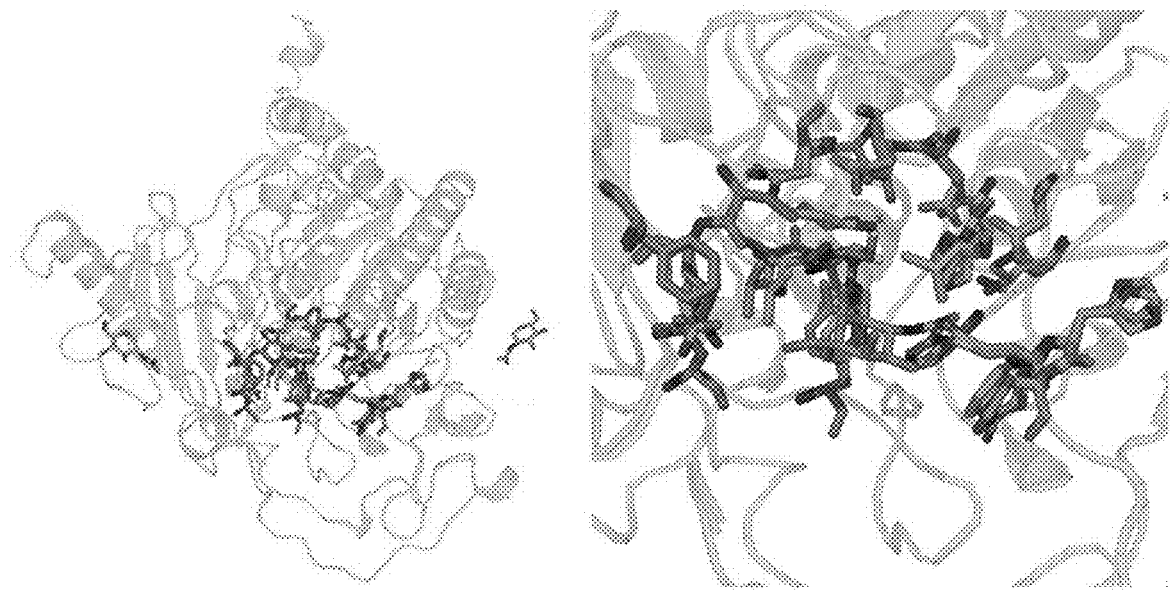
FIG. 3O Molecular docking visualization of modified peptide GALNS-231 superimposed onto GALNS.
Figure 4A:
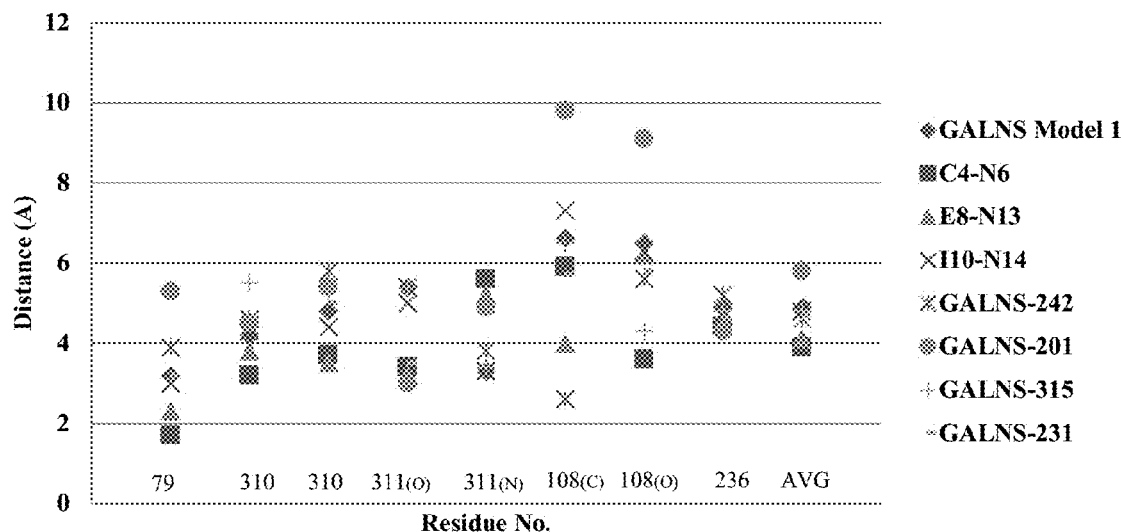
FIGS. 4A and 4B illustrate active site molecular docking. Distances in angstroms were measured between the active site residues (79, 310#1, 310#2, 311(O), 311(N), 108(C), 108(O), and 236) and the N-Acetyl-D-Galactosamine substrate (FIG. 4A). Distances in angstroms were measured between the active site residues (79, 39, 40, 288, 289) and the $Ca^{2+}$ within the active site (FIG. 4B).
Figure 4B:
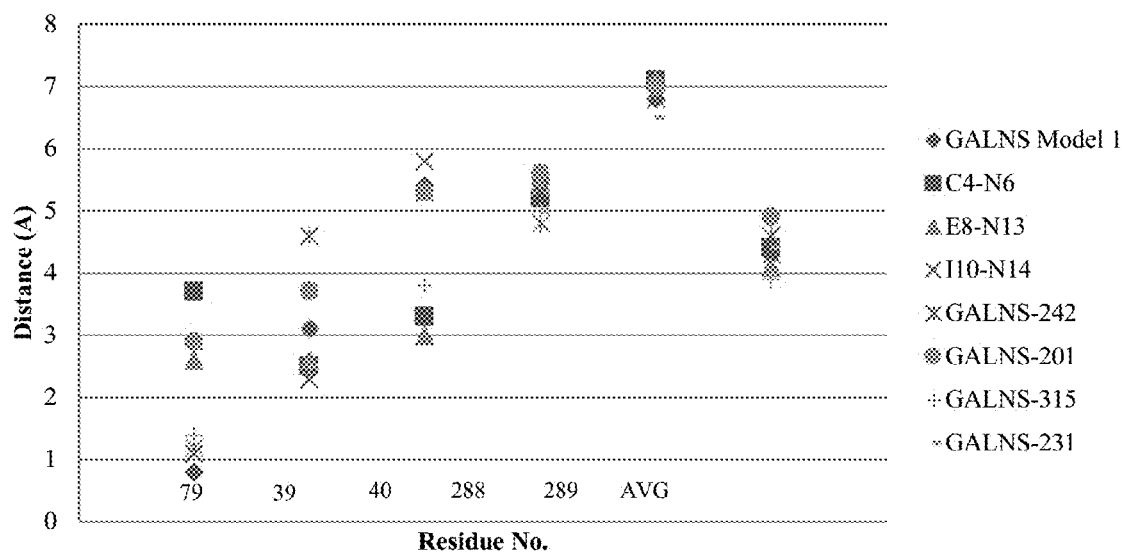

Working within these 3 immunodominant regions, the Inventors initially created 324 modified sequences, from which 92 modified sequences were initially selected after screening the sequences for predicted reduced immunogenicity using IEDB and RANKPEP analysis. More rigorous selection ultimately lead to 7 selected sequences. FIGS. 2A and 2B show IEDB and RANKPEP analysis respectively, for the final 7 selected sequences. The results from both IEDB and RANKPEP analysis, showed immunogenic variation associated with each amino acid change.

More specifically, these 7 sequences were selected as follows. From the 92 modified sequences, 21 sequences were further selected after consideration of in silico predictions of phosphorylation sites Table 1A), N-glycosylation sites (Table 1 B), and when the physic chemical properties of the modified sequences were compared to those of the original GALNS sequence (Table 1C).

TABLE 1A

Phosphorylation Predictions GALNS Amino Acid Sequence.

| Position | Code | GPS 2.1 Sequence | GPS 2.1 Score | Position | Code | NetPhos 2.0 Sequence | NetPhos 2.0 Score |
|---|---|---|---|---|---|---|---|
| 56 | T | YGEPSRETPNLDRMA (SEQ ID NO: 12) | 9.526 | 359 | S | LTPPSDRAI SEQ ID NO: 24 | 0.963 |
| 109 | T | AHARNAYTPQEIVGG (SEQ ID NO: 13) | 9.421 | 80 | S | NPLCSPSRA (SEQ ID NO: 25) | 0.903 |
| 181 | Y | ARPNIPVYRDWEMVG (SEQ ID NO: 14) | 9.4 | 466 | S | QEALSRITS (SEQ ID NO: 26) | 0.889 |
| 356 | T | SLALAGLTPPSDRAI (SEQ ID NO: 15) | 9.333 | 341 | S | HQLGSIMDL (SEQ ID NO: 27) | 0.882 |
| 181 | Y | ARPNIPVYRDWEMVG (SEQ ID NO: 14) | 9.333 | 264 | S | EIDDSIGKI (SEQ ID NO: 28) | 0.834 |
| 49 | Y | GWGDLGVYGEPSRET (SEQ ID NO: 16) | 9.333 | 470 | S | SRITSVVQQ (SEQ ID NO: 29) | 0.721 |
| 108 | Y | NAHARNAYTPQEIVG (SEQ ID NO: 17) | 9.25 | 458 | S | LSFASAEYQ (SEQ ID NO: 30) | 0.694 |
| 356 | T | SLALAGLTPPSDRAI (SEQ ID NO: 15) | 9.211 | 135 | S | AGYVSKIVG (SEQ ID NO: 31) | 0.63 |
| 49 | Y | GWGDLGVYGEPSRET (SEQ ID NO: 16) | 9.2 | 408 | S | TWTNSWENF (SEQ ID NO: 32) | 0.592 |
| 249 | S | SKPFLGTSQRGRYGD (SEQ ID NO: 18) | 9.1 | 56 | T | PSRETPNLD (SEQ ID NO: 33) | 0.959 |
| 109 | T | AHARNAYTPQEIVGG (SEQ ID NO: 13) | 9 | 389 | T | YRGDTLMAA (SEQ ID NO: 34) | 0.949 |
| 240 | Y | DATHAPVYASKPFLG (SEQ ID NO: 19) | 8.667 | 312 | T | CGKQTTFEG (SEQ ID NO: 35) | 0.832 |
| 470 | S | EALSRITSVVQQHQE (SEQ ID NO: 20) | 8.667 | 509 | T | GKCLTPPES (SEQ ID NO: 36) | 0.767 |
| 108 | Y | NAHARNAYTPQEIVG (SEQ ID NO: 17) | 8.667 | 469 | T | LSRITSVVQ (SEQ ID NO: 37) | 0.523 |

TABLE 1A-continued

Phosphorylation Predictions GALNS Amino Acid Sequence.

| Position | Code | GPS 2.1 Sequence | GPS 2.1 Score | Position | Code | NetPhos 2.0 Sequence | NetPhos 2.0 Score |
|---|---|---|---|---|---|---|---|
| 80 | S | YSANPLCSPSRAALL (SEQ ID NO: 21) | 8.667 | 240 | Y | HAPVYASKP (SEQ ID NO: 38) | 0.897 |
| 509 | T | EKLGKCLTPPESIPK (SEQ ID NO: 22) | 8.421 | 133 | Y | KKAGYVSKI (SEQ ID NO: 39) | 0.895 |
| 49 | Y | GWGDLGVYGEPSRET (SEQ ID NO: 16) | 8.286 | 98 | Y | RNGFYTTNA (SEQ ID NO: 40) | 0.87 |
| 80 | S | YSANPLCSPSRAALL (SEQ ID NO: 21) | 8.25 | 170 | Y | HFGPYDNKA (SEQ ID NO: 41) | 0.736 |
| 249 | S | SKPFLGTSQRGRYGD (SEQ ID NO: 18) | 8.111 | | | | |
| 469 | T | QEALSRITSVVQQHQ (SEQ ID NO: 23) | 8.1 | | | | |
| 356 | T | SLALAGLTPPSDRAI (SEQ ID NO: 15) | 8 | | | | |
| 509 | T | EKLGKCLTPPESIPK (SEQ ID NO: 22) | 8 | | | | |
| 469 | T | QEALSRITSVVQQHQ (SEQ ID NO: 23) | 8 | | | | |

Predicted sites of phosphorylation are identified by sequence position (Position) and amino acid identifying code (Code).

TABLE 1B

N-Glycosylation Predictions

| Sequence | Position | NetNGlyc 1.0 Sequence | Potential Agreement | Jury Result | N-Glyc |
|---|---|---|---|---|---|
| GALNS | 204 | NLTQ | 0.7763 | (9/9) | +++ |
| | 423 | NVSG | 0.5894 | (8/9) | + |
| GALNS-4 | 204 | NLTQ | 0.7762 | (9/9) | +++ |
| | 423 | NVSG | 0.5894 | (8/9) | + |

TABLE 1C

Physico-Chemical Properties

| Sequence | Molec. Wt | Theoretical pI | Instability Index (II) | Aliphatic Index (AI) | GRAVY |
|---|---|---|---|---|---|
| GALNS | 58026.0 | 6.25 | 35.37 | 80.61 | −0.250 |
| GALNS-4 | 58062.0 | 6.25 | 34.71 | 83.03 | −0.224 |

Sequences were selected if the modified sequence showed zero or insignificant changes when compared to the original GALNS sequence. By way of example, the original GALNS protein has 2 N-glycosylation sites, which were not changed in the modified proteins. Differences in physico-chemical properties between original GALNS and the modified peptides were insignificant. Several sequences were predicted to have an additional phosphorylation site at T235 and these sequences were also not selected. Sequences with an additional phosphorylation site were also not selected.

From these 21 sequences, 7 sequences were further selected, after molecular visualization analysis of ligand binding and molecular docking. Table 2 provides a summary of amino acid modifications in the final 7 sequences.

TABLE 2

Peptide modifications within immunogenic groups of GALNS 7 Selected Sequences

| Peptide Group | | Sequence | Peptide(s) |
|---|---|---|---|
| 1 Peptide | C4 | | C4-N bind. Modified sequences were chosen if their measured distances within the active site were very close to or even smaller than the measured distance in the original GALNS sequence. These results are summarized in Table 3a and Table 3b respectively.

Table 3 Distances from Active Site Atom to Substrate in Angstroms

TABLE 3(a)

N-Acetyl Galactosamine (NGA) active site.

| Sequence | Peptide(s) | NGA | | | | | | | | |
|---|---|---|---|---|---|---|---|---|---|---|
| | | 79 | 310 | 310 | 311(O) | 311(N) | 108(C) | 108(O) | 236 | AVG |
| GALNS Model 1 | — | 3.2 | 4.2 | 4.8 | 5.4 | 3.3 | 6.6 | 6.5 | 4.9 | 4.9 |
| C4-N6 | C4-N6 | 1.7 | 3.2 | 3.7 | 3.4 | 5.6 | 5.9 | 3.6 | 4.4 | 3.9 |
| E8-N13 | E8-N13 | 2.3 | 3.8 | 3.5 | 3.2 | 5.2 | 4.0 | 6.2 | 4.7 | 4.1 |
| I10-N14 | I10-N14 | 3.0 | 4.3 | 4.4 | 5.0 | 3.3 | 7.3 | 6.3 | 4.7 | 4.8 |
| GALNS-242 | C4-N7 + E8-N11 | 3.9 | 4.6 | 5.8 | 5.4 | 3.8 | 2.6 | 5.6 | 5.2 | 4.6 |
| GALNS-201 | C4-N6 + I10-N14 | 5.3 | 4.5 | 5.4 | 3.0 | 4.9 | 9.8 | 9.1 | 4.3 | 5.8 |
| GALNS-315 | E8-N14 + I10-N14 | 3.1 | 5.5 | 5.3 | 5.4 | 3.4 | 6.5 | 4.3 | 4.8 | 4.8 |
| GALNS-231 | C4-N6 + E8-N14 + I10-N14 | 3.2 | 4.6 | 5.0 | 3.5 | 4.8 | 5.7 | 5.8 | 4.6 | 4.7 |

TABLE 3(b)

Calcium active site.

| Sequence | Peptide(s) | $Ca^{2+}$ | | | | | |
|---|---|---|---|---|---|---|---|
| | | 79 | 39 | 40 | 288 | 289 | AVG |
| GALNS Model 1 | — | 0.8 | 3.1 | 5.4 | 5.5 | 6.8 | 4.3 |
| C4-N6 | C4-N6 | 3.7 | 2.5 | 3.3 | 5.2 | 7.1 | 4.4 |
| E8-N13 | E8-N13 | 2.6 | 2.6 | 3.0 | 5.4 | 7.1 | 4.1 |
| I10-N14 | I10-N14 | 1.1 | 2.3 | 5.8 | 5.3 | 6.8 | 4.3 |
| GALNS-242 | C4-N7 + E8-N11 | 1.2 | 4.6 | 5.3 | 4.8 | 6.9 | 4.6 |
| GALNS-201 | C4-N6 + I10-N14 | 2.9 | 3.7 | 5.3 | 5.6 | 7.0 | 4.9 |
| GALNS-315 | E8-N14 + I10-N14 | 1.4 | 2.4 | 3.8 | 5.0 | 7.0 | 3.9 |
| GALNS-231 | C4-N6 + E8-N14 + I10-N14 | 2.8 | 2.5 | 5.3 | 5.0 | 6.5 | 4.4 |

Corresponding cDNA sequences were then constructed for the selected 7 modified amino acid sequences by in vitro mutagenesis. Corresponding cDNAs were then transcribed using in vitro systems known in the art, by way of example as described in U.S. patent application Ser. No. 13/760,907 (published as U.S. Patent Pub. No. 2013/0202633), incorporated herein by reference in its entirety.

In addition, post-translational modifications are an important factor affecting enzyme expression and activity in vivo. It is known that GALNS is modified post-translationally by another enzyme, Sulfatase-modifying factor 1 (SUMF1). To confirm that post-translationally modifications are maintained as they occur in vivo, the modified GALNS enzymes were also expressed and secreted from COS-7 cells cotransfected with cDNA for SUMF1. (See Examples)

Enzyme activity may be assessed through various in vitro techniques, by way of example those described in the examples below, as well as those described in Tomatsu at al., (2007) Mol Genet Metab. May; 91(1):69-78. Modified GALNS with reduced immunogenicity may then be used to treat subjects with Morquio IVA, using methods also know in the art and also as described in U.S. patent application Ser. No. 13/760,907 (published as U.S. Patent Pub. No. 2013/0202633).

It is expected that any of the modified GALNS enzymes described herein may be used to treat subjects with mucopolysaccharidoses type IVA, including experimental animal subjects and human subjects. Currently, a form of GALNS, branded as VIMIZIM (elosulfase alfa injection, solution, concentrate) (BioMarin Pharmaceutical inc.) is used to treat MPS IVA. The recommended dose is 2 mg per kg given intravenously over a minimum range of 3.5 to 4.5 hours, based on infusion volume, once every week. (See VIMIZIM product insert, and "Briefing Document for The Endocrinologic And Metabolic Drugs Advisory Committee" (BioMarin Pharmaceutical Inc)). It is expected that these protocols may be followed using equivalent amounts of modified enzyme, adjusted for any differences in activity. The amount of modified enzyme administered may be increased as necessary to compensate for any reduction in enzyme activity as was observed in some of the modified enzymes in vitro.

It is expected that an effective amount may be from: 0.1 mg to 1.0 mg per kg, mg 1 to 2 mg per kg, 2 mg to 3 mg per kg, 3 mg to 4 mg per kg, 4 mg to 5 mg per kg, 5 mg to 6 mg per kg, 6 mg to 8 mg per kg, 8 mg to 10 mg per kg, 10 mg to 15 mg per kg, 15 mg to 20 mg per kg, 20 mg to 30 mg per kg, 30 mg to 40 mg per kg, 40 mg to 50 mg per kg, or 50 mg to 100 mg per kg, or 100 mg to 200 mg per kg or more. The effective dose may be given, daily, weekly, every two weeks, every four weeks, monthly or combinations thereof.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLES

Materials and Methods

Amino acid sequence substitutions. The FASTA format of the original GALNS amino acid sequence and modified GALNS amino acid sequences was utilized for all of the following in silico programs. In silico analyses were performed on new sequences harboring various combinations of amino acid substitutions within the 3 immunodominant peptide regions, C4, E8, and I10, within the wild GALNS sequence.

Sequences were created by altering one amino acid at a time within individual peptide regions C4, E8, and I10. Individual amino acids were changed based upon their polarity groups: amino acids with positively charged side chains, negatively charged side chains, polar uncharged side chains, and hydrophobic side chains; by way of example, alanine was changed to valine, leucine, isoleucine, and other amino acids with hydrophobic side chains. Additionally, cysteine was not modified because of its unique structure with sulfide bonding. Finally, amino acids were not changed to already known mutations of Morquio A disease. The least immunogenic single and multiple amino acid changes per peptide were selected. These sequences were then combined to create sequences with 2-3 changes within each peptide region, and then combined 1-3 of the mutated C4, E8 and I10 peptide regions until all possible combinations were made to yield a total of 324 mutated sequences.

Immunogenicity Predictions

Immune Epitope Database[7] (IEDB) and RANKPEP[8] predicted the immunogenicity of the T cell epitope to MHC II binding for the mouse allele H2-IAb of GALNS based upon different collections of previous studies' peptide-binding data sets. IEDB was used via the T Cell Epitope Prediction for Peptide binding to MHC Class II molecules. Here, the FASTA sequences were entered to predict the immunogenicity of Ff2-IAb allele mice by IEDB percentile rank. RANKPEP was used with MHC II and 1-Ab criteria, with the same mutated sequences that were entered in IEDB, to predict the immunogenicity by RANKPEP score. RANKPEP scores>9.0 were determined to be antigenic and were, therefore, excluded from further evaluation. A higher percentile rank indicated less immunogenicity for IEDB[7], and a lower score indicated less immunogenicity for RANKPEP[8].

Physico-Chemical Property Predictions

Group-based Prediction System version 2.1[9] (GPS 2.1) (also see Xue at al., (2011) Protein Engineering, Design & Selection vol. 24 no. 3 pp. 255-260) and NetPhos 2.0 server[10] (also see Blom et al., (1999) Journal of Molecular Biology: 294(5):1351-1362) determined possible predictions of phosphorylation sites. In GPS 2.1, all phosphorylation kinases were selected for the entered FASTA sequences. In NetPhos 2.0, a single sequence in FASTA format was entered and phosphorylation predictions were selected for tyrosine, serine, threonine, and graphics generation. A higher score according to GPS 2.1 and NetPhos 2.0 indicated that a predicted phosphorylation site was more probable. Criteria for selected sequences included no new or lost phosphorylation sites compared to the original GALNS sequence.

NetNGlyc 1.0[11] (see Center for Biological Sequence Analysis, Technical University of Denmark) (Gupta et al., (2002) Pacific Symposium on Biocomputing 7:310-322). predicted the N glycosylation sites by simply pasting the FASTA sequences into the server. These N glycosylation predictions were compared to the N-glycosylation predictions of the original GALNS sequence from NetNGlyc 1.0. Sequences were selected if there were no new or lost N-glycosylation sites compared to the original GALNS.

The FASTA sequences were entered into Expasy ProtParam[12] (see Gasteiger et al., (In) John M. Walker (ed): (2005) The Proteomics Protocols Handbook, Humana Press pp. 571-607) to analyze the physico-chemical properties compared to those of the original GALNS. These properties include molecular weight, theoretical pI, instability index, aliphatic index, and the grand average of hydropathicity (GRAVY). The lowest instability index indicated a more stable protein. The sequences with the most similar physico-chemical properties to the original GALNS sequence were selected.

PyMOL 3D Structural Analysis

I-TASSER[13] was used to produce the in silico 3D molecular crystallography of protein structure and functions. I-TASSER provided 5 possible models to predict the crystallized structure of the proteins. 1 of 5 models per mutated protein was selected based upon the C-score of the model number. C-score is a confidence score for estimating the quality of predicted models by I-TASSER. C-score is typically in the range 2-5 where a C-score of higher value signifies a model with a high confidence and vice-versa.

These structures were then visualized via PyMOL v1.1-eval[14] to analyze the molecular docking and ligand binding of the selected mutated sequences as compared to the structure and binding sites of the original GALNS protein. Mutated sequences were compared to the I-TASSER prediction of GALNS model 1 to maintain consistency within the same protein structure and function prediction server. The two substrates (1) N-acetyl-D-Galactosamine (NGA) and (2) calcium that bind to the active site of GALNS were utilized from the RCSB PDB protein data bank PDB code 4FDJ2 (Berman et al., (2000) Nuclide Acid Research 28: 235-343). Each mutated sequence was superimposed onto GALNS model land the PDB: 4FDJ substrates by aligning the structures on PyMOL. Amino acids within the GALNS active site were determined by selecting residues within 6 angstroms (Å) of the $Ca^{2+}$ and NGA. Of those amino acids, PyMOL predicted the polar bonds between amino acids and the substrates based upon, distance between atoms (3.4-4.0 Å) and angular cutoffs. These distances were measured between individual atoms of the binding site amino acids and the atoms of the substrate to compare those distances of the mutated proteins and the original GALNS model 1 protein structure. Restriction enzyme predictions.

Table 4 illustrates wild type GALNS (SEQ ID NO:1), including: the signal peptide at residues 1-26; immunodominant region C4 at residues 163-182; immunodominant region E8 at residues 226-245; and immunodominant region I10 at residues 473-492. Modified GALNS sequences (SEQ ID NO:2-SEQ ID NO:8) are designated according to the modified region(s) followed by the modification. Amino acid residues that have been substituted are indicated by both bold and underlining. The sequences in Table 4 represent polypeptides prior to post-translational modification.

TABLE 4

Wild type and modified amino acid sequences for GALNS with reduced immunogenicity. Immunodominant peptide regions are shaded. Modifications are bold and underlined.

```
Wild type GALNS (SEQ ID NO: 1)
MAAVVAATRWWQLLLVLSAAGMGASGAPQPPNILLLLMDDMGWGDLGVYGEPSR
ETPNLDRMAAEGLLFPNFYSANPLCSPSRAALLTGRLPIRNGFYTTNAHARNAYTPQ
EIVGGIPDSEQLLPELLKKAGYVSKIVGKWHLGHRPQFHPLKHGFDEWFGSPNCHF
GPYDNKARPNIPVYRDWEMVGRYYEEFPINLKTGEANLTQIYLQEALDFIKRQARHH
PFFLYWAVDATHAPVYASKPFLGTSQRGRYGDAVREIDDSIGKILELLQDLHVADNT
FVFFTSDNGAALISAPEQGGSNGPFLCGKQTTFEGGMREPALAWWPGHVTAGQVS
HQLGSIMDLFTTSLALAGLTPPSDRAIDGLNLLPTLLQGRLMDRPIFYYRGDTLMAAT
LGQHKAHFWTWTNSWENFRQGIDFCPGQNVSGVTTHNLEDHTKLPLIFHLGRDPG
ERFPLSFASAEYQEALSRITSVVQQHQEALVPAQPQLNVCNWAVMNWAPPGCEKL
GKCLTPPESIPKKCLWSH C4-N6 (SEQ ID NO: 2)
MAAVVAATRWWQLLLVLSAAGMGASGAPQPPNILLLLMDDMGWGDLGVYGEPSR
ETPNLDRMAAEGLLFPNFYSANPLCSPSRAALLTGRLPIRNGFYTTNAHARNAYTPQ
EIVGGIPDSEQLLPELLKKAGYVSKIVGKWHLGHRPQFHPLKHGFDEWFGSPNCHF
GPYDNKIRGQIPVYRDWEMVGRYYEEFPINLKTGEANLTQIYLQEALDFIKRQARHH
PFFLYWAVDATHAPVYASKPFLGTSQRGRYGDAVREIDDSIGKILELLQDLHVADNT
FVFFTSDNGAALISAPEQGGSNGPFLCGKQTTFEGGMREPALAWWPGHVTAGQVS
HQLGSIMDLFTTSLALAGLTPPSDRAIDGLNLLPTLLQGRLMDRPIFYYRGDTLMAAT
LGQHKAHFWTWTNSWENFRQGIDFCPGQNVSGVTTHNLEDHTKLPLIFHLGRDPG
ERFPLSFASAEYQEALSRITSVVQQHQEALVPAQPQLNVCNWAVMNWAPPGCEKL
GKCLTPPESIPKKCLWSH E8-N13 (SEQ ID NO: 3)
MAAVVAATRWWQLLLVLSAAGMGASGAPQPPNILLLLMDDMGWGDLGVYGEPSR
ETPNLDRMAAEGLLFPNFYSANPLCSPSRAALLTGRLPIRNGFYTTNAHARNAYTPQ
EIVGGIPDSEQLLPELLKKAGYVSKIVGKWHLGHRPQFHPLKHGFDEWFGSPNCHF
GPYDNKARPNIPVYRDWEMVGRYYEEFPINLKTGEANLTQIYLQEALDFIKRQARHH
PFFLIWAVDLTHLPVYASKPFLGTSQRGRYGDAVREIDDSIGKILELLQDLHVADNTF
VFFTSDNGAALISAPEQGGSNGPFLCGKQTTFEGGMREPALAWWPGHVTAGQVSH
QLGSIMDLFTTSLALAGLTPPSDRAIDGLNLLPTLLQGRLMDRPIFYYRGDTLMAATL
GQHKAHFWTWTNSWENFRQGIDFCPGQNVSGVTTHNLEDHTKLPLIFHLGRDPGE
RFPLSFASAEYQEALSRITSVVQQHQEALVPAQPQLNVCNWAVMNWAPPGCEKLG
KCLTPPESIPKKCLWSH I10-N14 (SEQ ID NO: 4)
MAAVVAATRWWQLLLVLSAAGMGASGAPQPPNILLLLMDDMGWGDLGVYGEPSR
ETPNLDRMAAEGLLFPNFYSANPLCSPSRAALLTGRLPIRNGFYTTNAHARNAYTPQ
EIVGGIPDSEQLLPELLKKAGYVSKIVGKWHLGHRPQFHPLKHGFDEWFGSPNCHF
GPYDNKARPNIPVYRDWEMVGRYYEEFPINLKTGEANLTQIYLQEALDFIKRQARHH
PFFLYWAVDATHAPVYASKPFLGTSQRGRYGDAVREIDDSIGKILELLQDLHVADNT
FVFFTSDNGAALISAPEQGGSNGPFLCGKQTTFEGGMREPALAWWPGHVTAGQVS
HQLGSIMDLFTTSLALAGLTPPSDRAIDGLNLLPTLLQGRLMDRPIFYYRGDTLMAAT
LGQHKAHFWTWTNSWENFRQGIDFCPGQNVSGVTTHNLEDHTKLPLIFHLGRDPG
ERFPLSFASAEYQEALSRITSVVQQHQEALVGIQGQLNVCNWAVMNWAPPGCEKL
GKCLTPPESIPKKCLWSH GALNS-201 (C4-N6 + I10-N14) (SEQ ID NO: 5)
MAAVVAATRWWQLLLVLSAAGMGASGAPQPPNILLLLMDDMGWGDLGVYGEPSR
ETPNLDRMAAEGLLFPNFYSANPLCSPSRAALLTGRLPIRNGFYTTNAHARNAYTPQ
EIVGGIPDSEQLLPELLKKAGYVSKIVGKWHLGHRPQFHPLKHGFDEWFGSPNCHF
GPYDNKIRGQIPVYRDWEMVGRYYEEFPINLKTGEANLTQIYLQEALDFIKRQARHH
PFFLYWAVDATHAPVYASKPFLGTSQRGRYGDAVREIDDSIGKILELLQDLHVADNT
FVFFTSDNGAALISAPEQGGSNGPFLCGKQTTFEGGMREPALAWWPGHVTAGQVS
HQLGSIMDLFTTSLALAGLTPPSDRAIDGLNLLPTLLQGRLMDRPIFYYRGDTLMAAT
LGQHKAHFWTWTNSWENFRQGIDFCPGQNVSGVTTHNLEDHTKLPLIFHLGRDPG
ERFPLSFASAEYQEALSRITSVVQQHQEALVGIQGQLNVCNWAVMNWAPPGCEKL
GKCLTPPESIPKKCLWSH GALNS-231 (C4-N6 + E8-N14 + I10-N14) (SEQ ID NO: 6)
MAAVVAATRWWQLLLVLSAAGMGASGAPQPPNILLLLMDDMGWGDLGVYGEPSR
ETPNLDRMAAEGLLFPNFYSANPLCSPSRAALLTGRLPIRNGFYTTNAHARNAYTPQ
EIVGGIPDSEQLLPELLKKAGYVSKIVGKWHLGHRPQFHPLKHGFDEWFGSPNCHF
GPYDNKIRGQIPVYRDWEMVGRYYEEFPINLKTGEANLTQIYLQEALDFIKRQARHH
PFFLIWAVDLTHIPVYASKPFLGTSQRGRYGDAVREIDDSIGKILELLQDLHVADNTFV
FFTSDNGAALISAPEQGGSNGPFLCGKQTTFEGGMREPALAWWPGHVTAGQVSH
QLGSIMDLFTTSLALAGLTPPSDRAIDGLNLLPTLLQGRLMDRPIFYYRGDTLMAATL
GQHKAHFWTWTNSWENFRQGIDFCPGQNVSGVTTHNLEDHTKLPLIFHLGRDPGE
RFPLSFASAEYQEALSRITSVVQQHQEALVGIQGQLNVCNWAVMNWAPPGCEKLG
KCLTPPESIPKKCLWSH GALNS-242 (C4-N7 + E8-N11) (SEQ ID NO: 7)
MAAVVAATRWWQLLLVLSAAGMGASGAPQPPNILLLLMDDMGWGDLGVYGEPSR
ETPNLDRMAAEGLLFPNFYSANPLCSPSRAALLTGRLPIRNGFYTTNAHARNAYTPQ
EIVGGIPDSEQLLPELLKKAGYVSKIVGKWHLGHRPQFHPLKHGFDEWFGSPNCHF
```

TABLE 4-continued

Wild type and modified amino acid sequences for GALNS with reduced immunogenicity. Immunodominant peptide regions are shaded. Modifications are bold and underlined.

GPYDNKLRGQIPVYRDWEMVGRYYEEFPINLKTGEANLTQIYLQEALDFIKRQARHH
PFFLIWLVDATHLPVYASKPFLGTSQRGRYGDAVREIDDSIGKILELLQDLHVADNTF
VFFTSDNGAALISAPEQGGSNGPFLCGKQTTFEGGMREPALAWWPGHVTAGQVSH
QLGSIMDLFTTSLALAGLTPPSDRAIDGLNLLPTLLQGRLMDRPIFYYRGDTLMAATL
GQHKAHFWTWTNSWENFRQGIDFCPGQNVSGVTTHNLEDHTKLPLIFHLGRDPGE
RFPLSFASAEYQEALSRITSVVQQHQEALVPAQPQLNVCNWAVMNWAPPGCEKLG
KCLTPPESIPKKCLWSH

GALNS-315 (E8-N14 + I10-N14) (SEQ ID NO: 8)
MAAVVAATRWWQLLLVLSAAGMGASGAPQPPNILLLLMDDMGWGDLGVYGEPSR
ETPNLDRMAAEGLLFPNFYSANPLCSPSRAALLTGRLPIRNGFYTTNAHARNAYTPQ
EIVGGIPDSEQLLPELLKKAGYVSKIVGKWHLGHRPQFHPLKHGFDEWFGSPNCHF
GPYDNKARPNIPVYRDWEMVGRYYEEFPINLKTGEANLTQIYLQEALDFIKRQARHH
PFFLIWAVDLTHIPVYASKPFLGTSQRGRYGDAVREIDDSIGKILELLQDLHVADNTFV
FFTSDNGAALISAPEQGGSNGPFLCGKQTTFEGGMREPALAWWPGHVTAGQVSH
QLGSIMDLFTTSLALAGLTPPSDRAIDGLNLLPTLLQGRLMDRPIFYYRGDTLMAATL
GQHKAHFWTWTNSWENFRQGIDFCPGQNVSGVTTHNLEDHTKLPLIFHLGRDPGE
RFPLSFASAEYQEALSRITSVVQQHQEALVGIQGQLNVCNWAVMNWAPPGCEKLG
KCLTPPESIPKKCLWSH

The FASTA format of the cDNA sequences were used for the determination of restriction enzyme sites and primer design via in silico programs. Finally, DNASIS MAX v3.0[15] predicted restriction enzyme sites; the FASTA format of the original GALNS cDNA sequence and modified sequences were used for DNASIS MAX v3.0. cDNA sequences were translated to the amino acid sequence from which the restriction enzyme cut map was determined. The GALNS and mutated sequences were compared to find the same restriction enzymes that cut at the same amino acid sequence.

Primer Design

QuikChange Primer Design[16] was used to computationally determine the primer sequences. Gene synthesis and mutagenesis of 7 selected sequences were ordered through GenScript.

Production of Modified Enzymes and Enzyme Activity

Corresponding cDNAs were then transcribed using in vitro systems. Seven modified GALNS enzymes were produced using standard cloning techniques and tested in vitro to determine GALNS activity.

Transfection: HEK-293 cells ($2.0\text{-}6.0\times10^4$ cells) were incubated with 1 μg of cDNA and 2 μl of Turbofect (ThermoFisher R0531)(cationic polymer in water). The media was changed after 4 hours and incubation continued for 72 hours. Media and cells were then washed 3 times with PBS. Di-deoxycholate (300 μl) was added, and the preparation centrifuged. A 30 μl aliquot of the pellet was assayed for GALNS activity and protein determination.

Enzyme Activity

GALNS activity was determined as described in Tomatsu at al., (2007) Mol Genet Metab. May; 91(1):69-78. pCXN, transfected with the plasmid vector alone represents background. Percent activity was calculated relative to wild type GALNS (100 percent).

TABLE 5

Enzyme activity is expressed as a percentage of wild type GALNS. (n = 3).

| Sample | Percent activity |
|---|---|
| C4-N6 | 32.004 |
| E8-N13 | 46.97 |
| I10-N14 | 40.647 |
| 201 | 64.093 |
| 242 | 84.82 |
| 315 | 81.014 |
| 231 | 90.448 |
| Wild type GALNS | 99.995 |
| p.CXN (Plasmid alone) | 43.271 |

Comparison of GALNS activity in modified GALNS enzymes, relative to wild type GALNS and p.CXN, indicates that GALNS modified with peptides 231, 242, 315, and 201, show acceptable functional activity (see Table 5).

Production of Modified Amino Acid Sequences for GALNS with Reduced Immunogenicity was Also Carried out in COS-7 Cells Co-Transfected with SUMF1.

To examine the effects amino acid substitutes on post-transcription modifications. Production of modified GALNS in COS-7 cells co-transfected was carried out as follows: COS-7 cells ($2.0\times10^5$ cells) were incubated with 4 μg of cDNA and 8 μl of Turbofect (ThermoFisher RO531)(cationic polymer in water). The media was changed after 4 hours and incubation continued for 72 hours. Media and cells were then washed 3 times with PBS. Di-deoxycholate (300 μl) was added, and the preparation was centrifuged. Double distilled $H_2O$ (30 μl) was added to the pellet and GALNS enzyme activity and protein were assayed as shown in FIG. 5 and Table 6.

TABLE 6

GALNS activity in modified peptides expressed
in COS-7 cells co-transfected with SUMF1.

| Pellet | Enzyme Activity U/mg | Percentage |
| --- | --- | --- |
| C4-N6 + SUMF1 | 0.576 | 443.08 |
| E8-N13 + SUMF1 | 0.737 | 566.92 |
| I10-N14 + SUMF1 | 0.738 | 567.69 |
| 201 + SUMF1 | 0.708 | 544.62 |
| 242 + SUMF1 | 0.564 | 433.85 |
| 315 + SUMF1 | 0.732 | 563.08 |
| 231 + SUMF1 | 0.817 | 628.46 |
| GALNS | 0.130 | 100.00 |
| GALNS + SUMF1 | 2.508 | 1929.23 |

Figure 5:
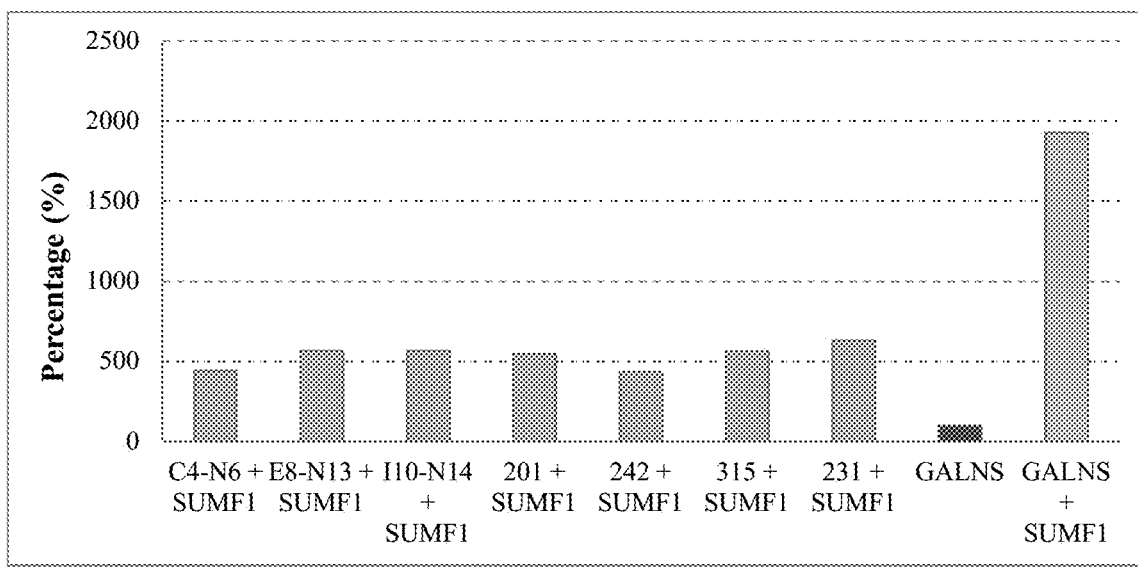
FIG. 5 illustrates GALNS activity in modified peptides produced in eukaryotic cells, which were co-transfected with Sulfatase-modifying factor 1 (SUMF1).

As illustrated in FIG. 5 and Table 6, modified GALNS enzymes have enhanced activity when produced in eukaryotic cells co-transfected with SUMF1.

In each of the following embodiments, and in the claims, the reference to percent GALNS activity is in reference to GALNS, and not in reference to GALNS+SUMF1, as shown in Table 6.

In one embodiment of the invention, is a modified GALNS enzyme where the amino acid Isoleucine is substituted at position 174, the amino acid Glycine is substituted at position 176, and the amino acid Glutamine is substituted at position 177, by way of non-limiting example, as set forth in SEQ ID NO:2.

In another embodiment of the invention is the sequence set forth in SEQ ID NO:2 secreted from a eukaryotic cell.

In another embodiment of the invention is a modified GALNS enzyme where the amino acid Isoleucine is substituted at position 229, the amino acid Leucine is substituted at position 234, and the amino acid Leucine is substituted at position 237, by way of non-limiting example, as set forth in SEQ ID NO:3.

In another embodiment of the invention is the sequence set forth in SEQ ID NO:3 secreted from a eukaryotic cell.

In another embodiment of the invention is a modified GALNS enzyme where the amino acid Glycine is substituted at position 481, the amino acid Isoleucine is substituted at position 482, and the amino acid Glycine is substituted at position 484, by way of non-limiting example, as set forth in SEQ ID NO:4.

In another embodiment of the invention is the sequence set forth in SEQ ID NO:4 secreted from a eukaryotic cell.

In another embodiment of the invention is a modified GALNS enzyme where the amino acid Isoleucine is substituted at position 174, the amino acid Glycine is substituted at position 176, the amino acid Glutamine is substituted at position 177, the amino acid Glycine is substituted at position 481, the amino acid Isoleucine is substituted at position 482, and the amino acid Glycine is substituted at position 484, by way of non-limiting example, as set forth in SEQ ID NO:5.

In another embodiment of the invention is the sequence set forth in SEQ ID NO:5 secreted from a eukaryotic cell.

In another embodiment of the invention, is a modified GALNS enzyme where the amino acid Isoleucine is substituted at position 174, the amino acid Glycine is substituted at position 176, the amino acid Glutamine is substituted at position 177, amino acid Isoleucine is substituted at position 229, the amino acid Leucine is substituted at position 234, the amino acid Isoleucine is substituted at position 237, the amino acid Glycine is substituted at position 481, the amino acid Isoleucine is substituted at position 482, and the amino acid Glycine is substituted at position 484, by way of non-limiting example, as set forth in SEQ ID NO:6.

In another embodiment of the invention is the sequence set forth in SEQ ID NO:6 secreted from a eukaryotic cell.

In another embodiment of the invention is a modified GALNS enzyme where the amino acid Leucine is substituted at position 174, the amino acid Glycine is substituted at position 176, the amino acid Glutamine is substituted at position 177, amino acid Isoleucine is substituted at position 229, the amino acid Leucine is substituted at position 234, and the amino acid Leucine is substituted at position 237, by way of non-limiting example, as set forth in SEQ ID NO:7.

In another embodiment of the invention is the sequence set forth in SEQ ID NO:7 secreted from a eukaryotic cell.

In yet another embodiment of the invention is a modified GALNS enzyme where amino acid Isoleucine is substituted at position 229, the amino acid Leucine is substituted at position 234, and the amino acid Isoleucine is substituted at position 237, the amino acid Glycine is substituted at position 481, the amino acid Isoleucine is substituted at position 482, and the amino acid Glycine is substituted at position 484, by way of non-limiting example, as set forth in SEQ ID NO:8.

In another embodiment of the invention is the sequence set forth in SEQ ID NO:8 secreted from a eukaryotic cell.

Additional embodiments of the invention include each of the above embodiments, secreted from a eukaryote cell, with 60 percent of more GALNS activity.

In yet another embodiment of the invention is a method of treating a subject with mucopolysaccharidoses type IVA, comprising: administering, intravenously, an effective amount of any of the modified N-acetylgalactosamine-6-sulfate sulfatase (GALNS) described herein, including but not limited to those set forth in SEQ ID NO:2, SEQ ID NO:3, SEQ ID NO:4, SEQ ID NO:5, SEQ ID NO:6, SEQ ID NO:7, or SEQ ID NO:8, and secreted from a eukaryote cell.

In yet another embodiment of the invention is a method of modifying proteins used in enzyme replacement therapy to treat subjects with lysosomal storage disorders to provide modified enzymes reduced immunogenic properties proteins.

It is recognized that the amino acid substitutions disclosed herein, made in wild type GALNS, are not limited to wild type GALNS, and may be in other variants or mutant forms of GALNS with equal or similar effectiveness.

Non-limiting examples of enzyme replacement therapy are described in U.S. patent application Ser. No. 13/760,907 (published as U.S. Patent Pub. No. 2013/0202633), incorporated herein by reference in its entirety. However, it is recognized that enzyme replacement therapy may be administered using other methodologies. By way of example, enzyme replacement therapy may be administered using methodology commonly known as gene therapy, wherein an oligonucleotide encoding the target enzyme is administered to the subject in such a manner that the target enzyme is expressed by the subject.

All publications and patents cited in this specification are hereby incorporated by reference in their entirety. The discussion of the references herein is intended merely to summarize the assertions made by the authors and no admission is made that any reference constitutes prior art. Applicants reserve the right to challenge the accuracy and pertinence of the cited references.

REFERENCES

1. Tomatsu S M A, Qikawa H, Smith M, Barrera L, Chinen Y, Thacker M M, Mackenzie W G, Suzuki V, OrH T.

Mucopolysaccharidosis type IVA (Morquio A disease): clinical review and current treatment. Curr Pharm Biotechnol. 2011; 12: 931-945.

2. Rivera-Colon Y S E, Kita A Z, Garman S C. The molecular basis of mucopolysaccharidosis IVA, complex with GalNac. J Mol Biol., 2012:736-751.

3. Montano A M T S, Gottesman G S, Smith M, Drii T. International Morquio A Registry: clinical manifestation and natural course of Morquio A disease. J Inherit Metab Dis. 2007:30: 165-1 74.

4. Tomatsu S M A, Dung V C, Ohashi A, Dikawa H, Oguma T, OrU T, Barrera L, Sly W S. Enhancement of Drug Delivery: Enzyme-replacement Therapy for Murine Morquio A Syndrome. Molecular Therapy. 2010:18: 1094-1102.

5. Hendriksz C, Burton, B., Fleming, T., Giugliani, R., Harmatz, P., Hughes, D., Jones, S., Lin, P., Mengel, K., Scarpa, M., Valayannopoulos, V. A multi-national, randomized, double-blind, placebo-controlled study to evaluate the efficacy and safety of BMN 110 treatment for mucopolysaccharidosis IVA (Morquio syndrome type A). Mol Genet Metab. 2013; 108: S17-5102.

6. Fireman M, DiMartini, A. F., Armstrong, S. C., Cozza, K. L. Immunosuppressants. Psychosomatics. 2004; 45: 354-360.

7. Nielsen M L C, Lund 0. Prediction of MHC class II binding affinity using SMM-align, a novel stabilization matrix alignment method. BMC Bioinformatics. 2007; 8.

8. Reche P A GJaRE. Prediction of MHC Class I Binding Peptides Using Profile Motifs. Human Immunology. 2002; 63: 701-709.

9. Xue Y R J, Gao X, Jin C, Wen L, Yao X. GPS 2.0, a Tool to Predict Kinase-specific Phosphorylation Sites in Hierarchy. Mol Cell Proteomics. 2008; 7: 1598-1 608.

10. Blom N, Gammeltoff, S., Brunak, S. Sequence- and structure-based prediction of eukaryotic protein phosphorylation sites. Journal of Molecular Biology. 1999; 294: 1351-1362.

11. Gupta R, Jung, E., and Brunak, S. Prediction of N-glycosylation sites in human proteins, unpublished. 2004.

12. Gasteiger E. H C, Gattiker A., Duvaud S., Wilkins M. R., Appel R. D., Bairoch A. Protein Identification and Analysis Tools on the ExPASy Server; (In) John M. Walker (ed): The Proteomics Protocols Handbook, Humana Press. 2005: 57-607.

13. Zhang Y. 1-TASSER server for protein 3D structure prediction. BMC Bioinformatics. 2008; 9.

14. The PyMOL Molecular Graphics System, Version 1.5.0.4 Schrödinger, LLC.

15. DNASIS MAX, Version 3.0. Hitachi Solutions America, Ltd. MiraiBio Group.

16. A. Novoradovsky VZ, M. Ghosh, H. Hogrefe, J. A. Sorge and T. Gaasterland. Computational Principles of Primer Design for Site Directed Mutagenesis. Nanotech. 2005; 1: 532-535.

---

What is claimed is:

1. A modified N-acetylgalactosamine-6-sulfate sulfatase (GALNS) with reduced immunogenic properties compared to wild type GALNS and having at least 60 percent GALNS activity as compared to wild type GALNS, wherein said GALNS is selected from the group consisting of: SEQ ID NO: 2, SEQ ID NO: 3, SEQ ID NO: 4, SEQ ID NO: 5, SEQ ID NO: 6, SEQ ID NO: 7 and SEQ ID NO: 8.

2. A modified N-acetylgalactosamine-6-sulfate sulfatase (GALNS) produced by a method comprising: transfecting a cell with a nucleic acid encoding the modified N-acetylgalactosamine-6-sulfate sulfatase (GALNS); and culturing the cell under conditions wherein the cell produces the modified GALNS, wherein said modified GALNS is selected from the group consisting of: SEQ ID NO:2, SEQ ID NO:3, SEQ ID NO:4, SEQ ID NO:5, SEQ ID NO:6, SEQ ID NO:7, and SEQ ID NO:8.

3. The modified GALNS of claim 2, wherein the cell is a eukaryotic cell.

4. The modified GALNS of claim 2, wherein the cell is a prokaryotic cell.

5. The modified GALNS of claim 2, wherein the modified GALNS is secreted from the cell.

6. The modified GALNS of claim 2 further comprising assaying the modified GALNS for GALNS activity.

7. The modified GALNS of claim 2 further comprising analyzing the modified GALNS for immunogenicity.

8. The modified GALNS of claim 2, wherein the modified GALNS has at least 60 percent GALNS activity as compared to wild type GALNS.

9. The modified GALNS of claim 2, wherein the modified GALNS has at least 80 percent GALNS activity as compared to wild type GALNS.

* * * * *